(12) United States Patent
McConnell et al.

(10) Patent No.: US 7,192,722 B2
(45) Date of Patent: Mar. 20, 2007

(54) PHENETHANOLAMINE-DERIVED HAPTENS, IMMUNOGENS, ANTIBODIES AND CONJUGATES

(75) Inventors: Robert Ivan McConnell, Ballymena (GB); Stephen Peter Fitzgerald, Crumlin (GB); El Ouard Benchikh, Antrim (GB); Andrew Philip Lowry, Belfast (GB)

(73) Assignee: Randox Laboratories, Crumlin (GB)

( * ) Notice: Subject to any disclaimer, the term of this patent is extended or adjusted under 35 U.S.C. 154(b) by 49 days.

(21) Appl. No.: 11/271,282

(22) Filed: Nov. 10, 2005

(65) Prior Publication Data
US 2006/0223132 A1     Oct. 5, 2006

(30) Foreign Application Priority Data
Nov. 10, 2004   (EP)   .................................. 04078100

(51) Int. Cl.
| G01N 33/53 | (2006.01) |
| G01N 33/532 | (2006.01) |
| G01N 33/533 | (2006.01) |
| C07K 1/10 | (2006.01) |
| C07K 1/13 | (2006.01) |
| C07K 1/04 | (2006.01) |
| C07K 16/00 | (2006.01) |

(52) U.S. Cl. ..................... 435/7.1; 435/7.92; 435/7.93; 435/975; 436/544; 436/546; 436/56; 530/402; 530/403; 530/388.9; 530/389.8

(58) Field of Classification Search .................. 435/7.1, 435/7.92, 7.93, 975; 436/544, 546, 56; 530/402, 530/403, 388.9, 389.8
See application file for complete search history.

(56) References Cited

U.S. PATENT DOCUMENTS 6,274,334 B1    8/2001   Shelver et al. ............. 435/7.92

OTHER PUBLICATIONS

Elliot, C.T. et al., "Screening and Confirmatory Determination of Ractopamine Residues in Calves Treated with Growth Promoting Doses of the β-Agonist", *Analyst*, May 1998, 123, 1103-1107.

(Continued)

*Primary Examiner*—Long V. Le
*Assistant Examiner*—Shafiqul Haq
(74) *Attorney, Agent, or Firm*—Woodcock Washburn LLP

(57) ABSTRACT

The present invention relates to a method for preparing haptens of formulae I and II that are useful in the preparation of immunogens, antibodies and conjugates, for use in competitive immunoassays for the detection of ractopamine, isoxsuprine and ritodrine. The haptens are prepared by reacting a phenylethanolamine derivative of formula D with a phenylalkylcarbonyl derivative of formula E:

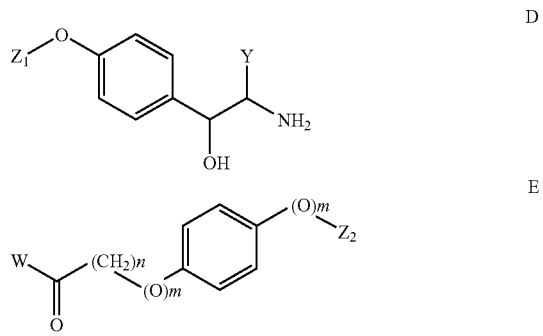

in which, in formula I, $Z_1$ is a crosslinker and $Z_2$ is H and, in formula II, $Z_1$ is H and $Z_2$ is a crosslinker.

27 Claims, 7 Drawing Sheets

Chemical structures of Ractopamine, Ritodrine and Isoxsuprine

Ractopamine

Ritodrine

Isoxsuprine

OTHER PUBLICATIONS

Haasnoot, W. et al., "Determination of Fenoterol and Ractopamine in Urine by Enzyme Immunoassay", *Analyst*, 1994, 119, 2675-2680.

Lommen, A. et al., "Nuclear Magnetic Resonance Controlled Method for Coupling of Fenoterol to a Carrier and Enzyme", *Food & Agricultural Immunology*, 1995, 7, 123-129.

Shelver, W.L. et al., "Production and Characterization of Monoclonal Antibody against the β-Adrenergic Agonist Ractopamine", *J. Agric. Food Chem*, 2000, 48, 4020-4026.

Shelver, W.L. et al., "Development of an Immunoassay for the β-Adrenergic Agonist Ractopamine", *Journal of Immunoassay*, 2000, 21(1), 1-23.

Shelver, W.L. et al., "Determination of Ractopamine in cattle and Sheep Urine Samples Using an Optical Biosensor Analysis: Comparative Study with HPLC and ELISA", *J. Agric. Food Chem*, 2003, 51, 3715-3721.

Siegel, M.G. et al., "The Use of High-Throughput Synthesis and Purification in the Preparation of a Directed Library of Adrenergic Agents", *Molecular Diversity*, 1998, 3, 113-116.

Smith, D.J. et al., "issue Residues of Ractopamine and Urinary Excretion of Ractopamine and Metabolites in Animals Treated for 7 Days with Dietary Ractopamine", *J. Anim. Sci.*, 2002, 80, 1240-1249.

Haasnoot, W. et al., "Immunofiltration as Sample Cleanup for the Immunochemical Detection of β-Agonists in Urine", *Analyst, The Royal Society of Chemistry*, 2002, 127, 87-92.

Madding, G.D., "Synthesis of Tritium Labeled Isoxsuprine Hydrochloride", *Journal of Labeled Compounds*, 1971, 7(4), 393-397.

Ren, J.Z. et al., "Synthesis of Ritodrine", *Zhongguo Yiyao Gongye Zazhi*, 2000, 31(6), 241-242.

Shelver, W.L. et al., "Application of a Monoclonal Antibody-Based Enzyme-Linked Immunosorbent Assay for the Determination of Ractopamine in Incurred Samples from Food Animals", *J. Aric. Food Chem.*, 2002, 50, 2742-2747.

Terando, N.H., "Synthesis of 14C-Radiolabeled Ractopamine Hydrochloride", *Journal of Labelled Compounds and Radiopharmaceuticals*, 1992, 31(9), 651-658.

Chemical structures of Ractopamine, Ritodrine and Isoxsuprine

Ractopamine

Ritodrine

Isoxsuprine

Chemical Structure of Haptens A, B, C, D, and E

Chemical reactions for the preparation of Hapten B and Immunogen B

Chemical reactions for the preparation of Hapten C and Immunogen C

Chemical reactions for the preparation of Hapten D and Immunogen D

Chemical reactions for the preparation of Hapten E and Immunogen E

PHENETHANOLAMINE-DERIVED HAPTENS, IMMUNOGENS, ANTIBODIES AND CONJUGATES

FIELD OF THE INVENTION

The present invention relates to a method for preparing haptens that are useful for the preparation of immunogens, antibodies and conjugates, for use in competitive immunoassays for the detection of phenethanolamines such as, but not limited to, ractopamine, isoxsuprine and ritodrine. The present invention also relates to a method and kit for detecting or determining phenethanolamines such as, but not limited to, ractopamine, isoxsuprine and ritodrine.

BACKGROUND OF THE RELATED ART

By "detecting" is meant qualitatively analysing for the presence or absence of a substance. By "determining" is meant quantitatively analysing for the amount of a substance.

Ractopamine is a phenethanolamine leanness-enhancing agent recently approved as a feed additive for swine in the United States. Hogs administered dietary ractopamine show increased growth rates and feed efficiencies and decreased fat deposition, relative to untreated animals.

Phenethanolamine β-agonists have a history of being used for off-label purposes by livestock producers hoping to improve the economics of livestock production. Improper use of β-agonists can cause a serious risk to human health due to the residues they leave in the meat and other foodstuffs of animal origin. Indeed, in Europe, all β-agonists are banned for use in livestock and for improving athletic performance under EU Directive 96/22/EC.

The presence of drug residues in animal tissues is a concern for food safety, especially when the compound has been used illegally or in a manner proscribed by regulatory officials (off-label use). In an effort to combat such illicit use of β-agonist compounds, regulatory organisations around the world test animal tissues and body fluids for the presence of such illicit drugs.

Specific binding actions, such as antibody-antigen interactions, have been used extensively in immunoassays to detect a variety of substances present in biological fluids. Thus, for example, radioimmunoassays could be used for the determination of phenethanolamines such as ractopamine, isoxsuprine and ritodrine. Radioimmunoassays are very sensitive but do require radionucleotide tracers. Enzyme-linked immunosorbent assays (ELISAs) are a non-radioactive alternative which could be used for the qualitative and quantitative determination of phenethanolamines such as, but not limited to, ractopamine, isoxsuprine and ritodrine.

Haasnoot et al (The Analyst (1994), 119, "Determination of fenoterol and ractopamine in urine by enzyme immunoassay", 2675–2680) disclose a urinary enzyme immunoassay for ractopamine. The Haasnoot antibody was derived from a fenoterol derivative and showed 20% cross-reactivity with ractopamine, but the analysis of ractopamine did not correlate well with GC-MS analysis. Elliott et al (The Analyst (1998), 123, "Screening and confirmatory determination of ractopamine residues in calves treated with growth promoting doses of the β-agonist", 1103–1107) disclose an immunoassay for ractopamine residues. The Elliott antibody, when used in an immunoassay where the samples were enzymatically hydrolysed prior to analysis, correlated well with LC-MS-MS but, as with Haasnoot et al, the antibodies were raised in a non-targeted fashion, against a fentoterol derivative.

Shelver and Smith (Journal of Immunoassay (2000), 21(1), "Development of an immunoassay for the β-adrenergic agonist ractopamine", 1–23) disclose preparation of polyclonal antibodies generated from ractopamine-hemiglutarate-KLH. The hapten is prepared by reaction of ractopamine with glutaric anhydride, followed by conjugation with an antigenicity-conferring carrier material. The method employed to synthesize ractopamine-hemiglutarate is uncontrolled and will result in derivatisation of ractopamine at any one of positions 1, 10, 10' and N. The Shelver and Smith antibody generated shows a sensitivity ($IC_{50}$) of 4.2 ng/ml toward ractopamine. The antibody also exhibits 33% cross-reactivity with dobutamine.

Shelver et al (J. Agric. Food Chem. 48 (2000), "Production and characterisation of a monoclonal antibody against the β-adrenergic agonist ractopamine", 4020–4026 and their U.S. Pat. No. 6,274,334) disclose the generation of a monoclonal antibody, in which ractopamine-glutarate-keyhole limpet haemocyanin was used as the antigen for antibody generation. The antibody clone selected (5G10) shows 5.3% cross-reactivity with dobutamine and 3.6% cross-reactivity with ritodrine.

A polyclonal antibody is generated by repeated immunisation of a mammalian host with the target immunogen. The resulting antiserum is harvested and the antibodies isolated. To generate a monoclonal antibody, lymphocytes from an immunized animal are fused with a myeloma cell line to produce hybrid cells or hybridomas. These hybridomas can be cloned for production of the secreted monoclonal antibody. A monoclonal antibody will recognize a single epitope, whereas a polyclonal antiserum may recognize several epitbpes on the same antigen. Hence, monoclonal antibody technology can usually be applied to generate an antibody with greater specificity for the target immunogen.

In the aforementioned Shelver et al, a 'scattergun' approach has been used to generate polyclonal antibodies to ractopamine. The uncontrolled method used to prepare the ractopamine hapten suggests that the resulting immunogen is composed of a mixture of ractopamine linked to keyhole limpet haemocyanin (KLH) at any one of positions 1, 10, 10' and N. Immunisation with such an immunogen will result in the generation of antisera with a diversity of specificity. This is borne out in the cross-reactivity data presented in the Shelver reference. Their polyclonal antibody cross-reacts 33% with dobutamine, while their monoclonal antibody cross-reacts 5.3% with dobutamine. In contrast, the targeted introduction of a crosslinker group onto a single phenolic hydroxyl group of the target hapten, according to the present invention, produces a surprising effect (a heterofunctional crosslinker as defined herein, is a structure incorporating one or more functional groups containing one or more heteroatoms, that links, for example through covalent bonding, with a substrate (in this case a hapten), the crosslinker also being able to link to a peptide, polypeptide or protein or a detectable labelling agent). Antibodies generated to the present haptens are highly specific and do not cross-react significantly with dobutamine. In the case of ractopamine, the antibody generated to the position 10 derivative cross-reacts 0.186% with dobutamine, while the antibody generated to the position 10' derivative exhibits cross-reactivity of <0.8% with dobutamine. The only explanation for the cross-reactivity of the Shelver antibodies with dobutamine is that Shelver et al have generated antibodies to ractopamine derivatised at the position 1 hydroxyl (hydroxyl group on the aliphatic chain). This hydroxyl group is absent in dobutamine. The presence of a single hydroxyl group on one of the aromatic rings of the hapten derivatives used in the present application results in a high degree of specificity for ractopamine, isoxsuprine and ritodrine. The antibodies of the present application are also considerably more sensitive than the Shelver polyclonal and monoclonal antibodies. For ractopamine, the antibody to the position 10 derivative has an $IC_{50}$ of 0.082 ng/ml, while the antibody to the position 10' derivative has an $IC_{50}$ of 0.202 ng/ml. The present antibodies exhibit improved specificity and sensitivity. The present application illustrates how a superior antibody can be generated using polyclonal antibody technology and the process of targeted derivatisation.

None of the prior art known to the inventors either discloses or suggests preparing phenethanolamines haptens such as, but not limited to, ractopamine, isoxsuprine or ritodrine haptens by the method disclosed herein. The present method allows for the controlled coupling of a crosslinking group to a single phenolic hydroxyl group of the hapten. The present invention, by allowing the preparation of haptens and, therefore, immunogens derivatised at a single phenolic hydroxyl group, facilitates preparation of antibodies to immunogens derivatised at a single phenolic hydroxyl group. None of the prior art discloses or suggests targeted derivatisation of phenethanolamines such as, but not limited to, ractopamine, isoxsuprine and ritodrine analogues at a single phenolic hydroxy group. Such haptens also form part of the present invention.

SUMMARY OF THE INVENTION

The invention provides a method of preparing a hapten of formula I:

Hapten I

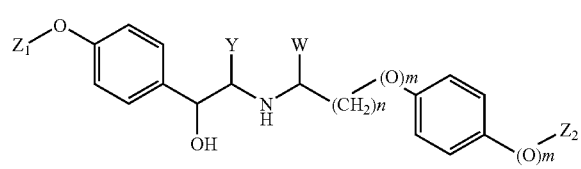

which is suitable for use in raising an antibody capable of binding with at least one structural epitope of a phenethanolamine. The method comprises the step of reacting a phenethanolamine derivative of formula D, in which $Z_1$ is a crosslinker, with a phenylalkylcarbonyl derivative of formula E, in which $Z_2$ is H; Y is independently H or $CH_3$; W is independently H or $CH_3$; n is independently 1 or 2; and m is independently 0 or 1.

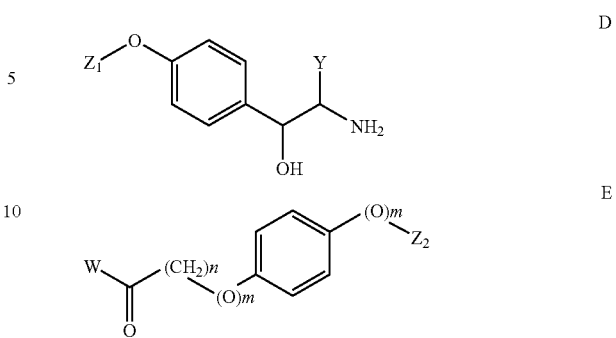

The phenethanolamine derivative of formula D may be prepared, for example, by reacting octopamine hydrochloride with $Z_1X_1$, in which $X_1$ is a halide. The amine group of the octapamine hydrochloride may be temporarily protected with BOC, by reacting the octapamine hydrochloride with di-tert-butyldicarbonate before reacting the BOC-protected octapamine hydrochloride with the $Z_1X_1$, the BOC group being subsequently removed.

The invention also provides a method of preparing a hapten of formula II:

Hapten II

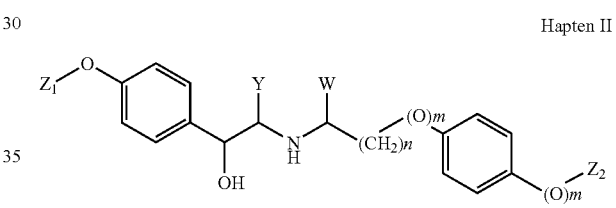

which is suitable for use in raising an antibody capable of binding with at least one structural epitope of a phenethanolamine. The method comprises the step of reacting a phenethanolamine derivative of formula D, in which $Z_1$ is H, with a phenylalkylcarbonyl derivative of formula E, in which $Z_2$ is a crosslinker; Y is independently H or $CH_3$; W is independently H or $CH_3$; n is independently 1 or 2; and m is independently 0 or 1.

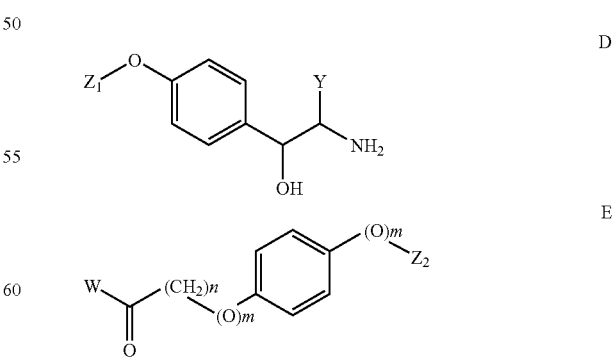

The phenylalkylcarbonyl derivative of the formula E may be prepared, for example, by reacting 4-(4-hydroxyphenyl)-2-butanone with $Z_2X_1$, in which $X_1$ is a halide.

The invention further provides a hapten derivatised with a crosslinker at $Z_1$, in which the hapten has the structural formula I:

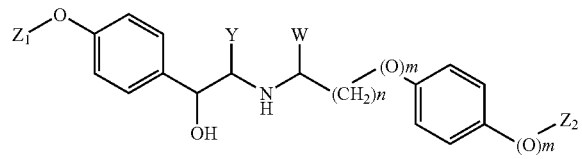

in which $Z_1$ is a crosslinker and $Z_2$ is H; Y is independently H or $CH_3$; W is independently H or $CH_3$; n is independently 1 or 2; and m is independently 0 or 1.

The invention still further provides a hapten derivatised with a crosslinker at $Z_2$, in which the hapten has the structural formula II:

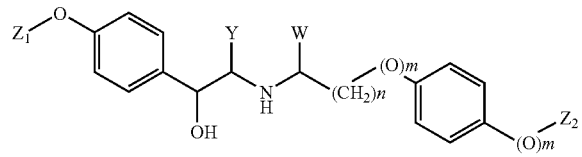

in which $Z_1$ is H and $Z_2$ is a crosslinker; Y is independently H or $CH_3$; W is independently H or $CH_3$; n is independently 1 or 2; and m is independently 0 or 1.

The invention also provides an immunogen comprising a hapten of structural formula I, coupled to an antigenicity-conferring carrier material. The invention further provides an antibody raised against the immunogen wherein the antibody is capable of binding at least one structural epitope of a phenethanolamine. The invention also provides a hapten conjugated to a detectable labelling agent.

The invention also provides an immunogen comprising a hapten of structural formula II, coupled to an antigenicity-conferring carrier material. The invention further provides an antibody raised against the immunogen wherein the antibody is capable of binding at least one structural epitope of a phenethanolamine. The invention also provides a hapten conjugated to a detectable labelling agent.

The invention still further provides a method for detecting or determining a phenethanolamine such as, but not limited to, ractopamine, isoxsuprine or ritodrine in a sample, the method comprising contacting the sample with at least one conjugate of the hapten of formula I conjugated to a detectable labelling agent, and with at least one antibody raised against the immunogen comprising the hapten of structural formula I coupled to an antigenicity-conferring carrier material; detecting or determining bound conjugate; and deducing from the calibration curve the presence of, or the amount of, the phenethanolamine in the sample.

The invention still further provides a method for detecting or determining a phenethanolamine such as, but not limited to, ractopamine, isoxsuprine or ritodrine in a sample, the method comprising contacting the sample with at least one conjugate of the hapten of formula I conjugated to a detectable labelling agent, and with at least one antibody raised against the immunogen comprising the hapten of structural formula II coupled to an antigenicity-conferring carrier material; detecting or determining bound conjugate; and deducing from the calibration curve the presence of, or the amount of, the phenethanolamine in the sample.

The invention still further provides a method for detecting or determining a phenethanolamine such as, but not limited to, ractopamine, isoxsuprine or ritodrine in a sample, the method comprising contacting the sample with at least one conjugate of the hapten of formula II conjugated to a detectable labelling agent, and with at least one antibody raised against the immunogen comprising the hapten of structural formula I coupled to an antigenicity-conferring carrier material; detecting or determining bound conjugate; and deducing from the calibration curve the presence of, or the amount of, the phenethanolamine in the sample.

The invention still further provides a method for detecting or determining a phenethanolamine such as, but not limited to, ractopamine, isoxsuprine or ritodrine in a sample, the method comprising contacting the sample with at least one conjugate of the hapten of formula II conjugated to a detectable labelling agent, and with at least one antibody raised against the immunogen comprising the hapten of structural formula II coupled to an antigenicity-conferring carrier material; detecting or determining bound conjugate; and deducing from the calibration curve the presence of, or the amount of, the phenethanolamine in the sample.

The invention also provides a kit for detecting or determining a phenethanolamine such as, but not limited to, ractopamine, isoxsuprine or ritodrine, the kit including at least one conjugate of the hapten of structural formula I conjugated to a detectable labelling agent; and at least one antibody raised against a hapten of structural formula I coupled to an antigenicity-conferring carrier material.

The invention also provides a kit for detecting or determining a phenethanolamine such as, but not limited to, ractopamine, isoxsuprine or ritodrine, the kit including at least one conjugate of the hapten of structural formula I conjugated to a detectable labelling agent; and at least one antibody raised against a hapten of structural formula II coupled to an antigenicity-conferring carrier material.

The invention also provides a kit for detecting or determining a phenethanolamine such as, but not limited to, ractopamine, isoxsuprine or ritodrine, the kit including at least one conjugate of the hapten of structural formula II conjugated to a detectable labelling agent; and at least one antibody raised against a hapten of structural formula I coupled to an antigenicity-conferring carrier material.

The invention also provides a kit for detecting or determining a phenethanolamine such as, but not limited to, ractopamine, isoxsuprine or ritodrine, the kit including at least one conjugate of the hapten of structural formula II conjugated to a detectable labelling agent; and at least one antibody raised against a hapten of structural formula II coupled to an antigenicity-conferring carrier material.

DETAILED DESCRIPTION OF THE ILLUSTRATIVE EMBODIMENTS

Figure 1:
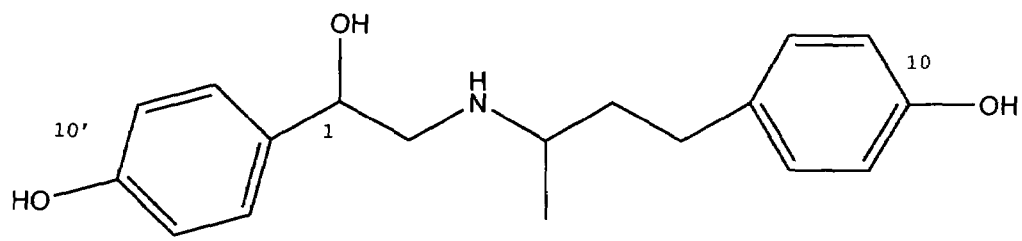
FIG. 1 shows the structures of ractopamine, ritodrine and isoxsuprine.
Figure 1:
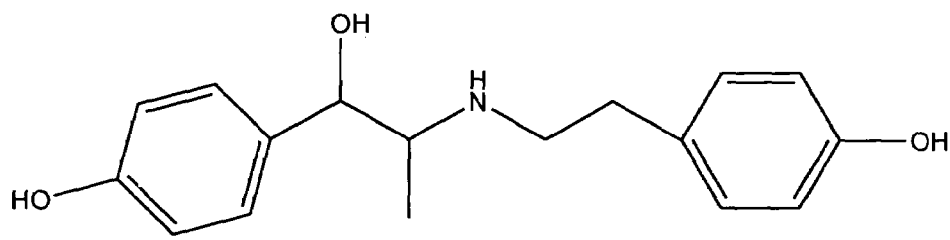
Figure 1:
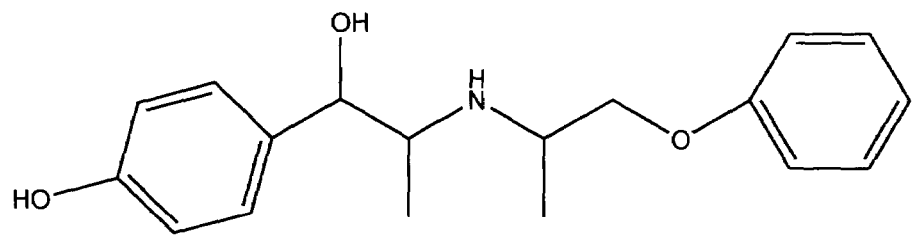

The present invention describes biaromatic haptens derivatised with crosslinkers at a single phenolic hydroxyl group. The structures of ractopamine, isoxsuprine and ritodrine are illustrated in FIG. 1.

The invention also provides a hapten derivatised with a crosslinker at $Z_1$, in which the hapten has the structural formula I

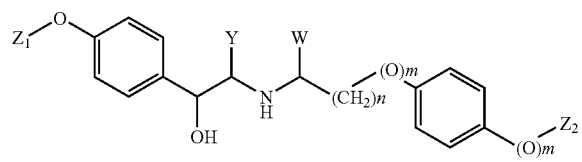

in which $Z_1$ is a crosslinker and $Z_2$ is H; Y is independently H or $CH_3$; W is independently H or $CH_3$; n is independently 1 or 2; and m is independently 0 or 1. Additionally, the invention provides a hapten derivatised with a crosslinker at $Z_2$, in which the hapten has the structural formula II

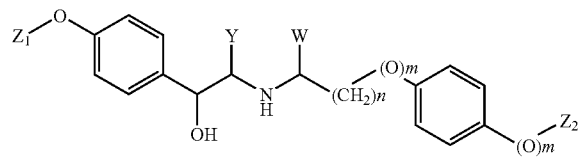

in which $Z_1$ is H and $Z_2$ is a crosslinker; Y is independently H or $CH_3$; W is independently H or $CH_3$; n is independently 1 or 2; and m is independently 0 or 1.

Figure 2:
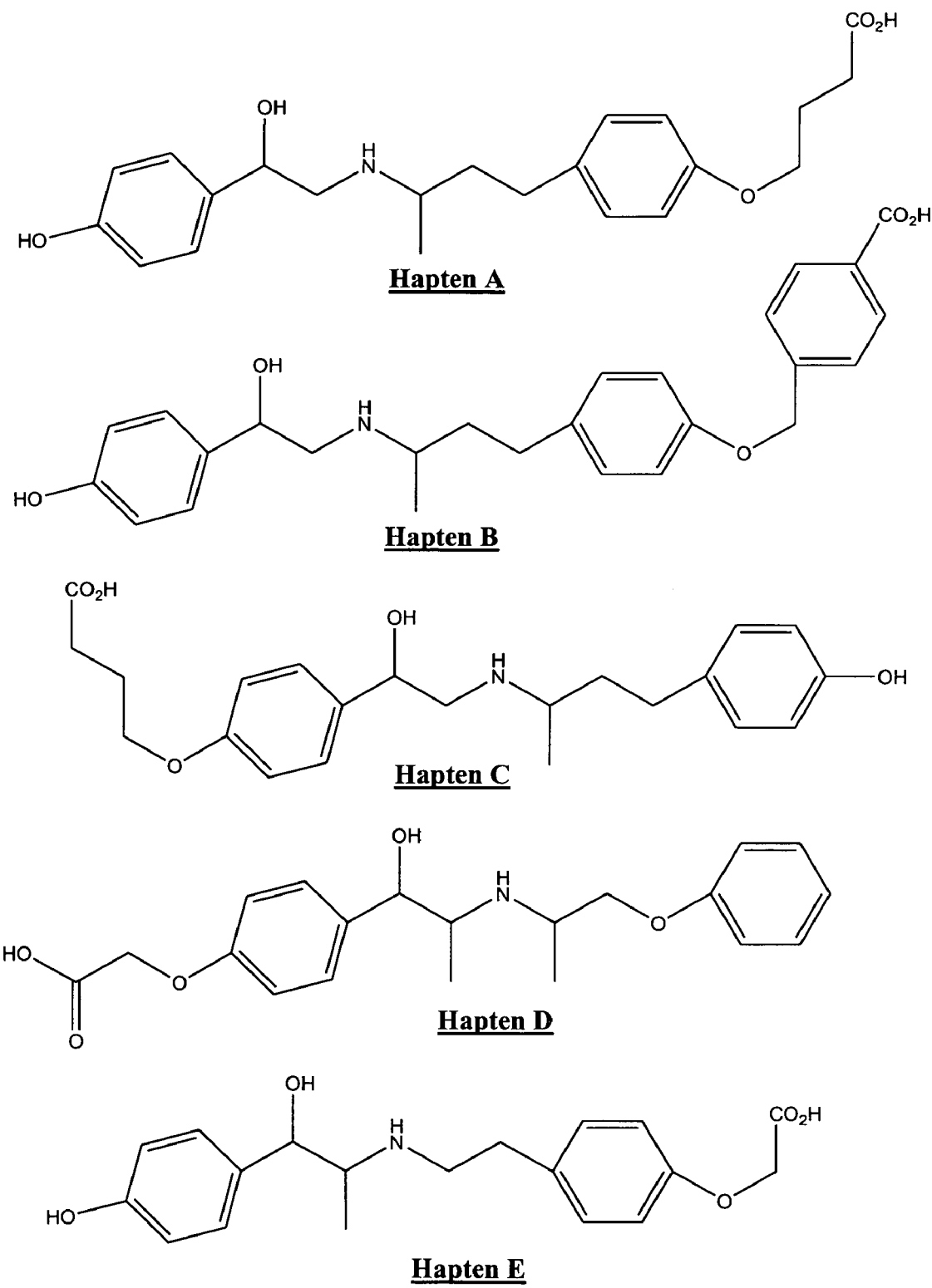
FIG. 2 shows the structures of Haptens A, B, C, D and E.

More preferably, the haptens have structural formulae A, B, C, D or E as illustrated in FIG. 2.

In a further aspect, the invention provides a method of preparing a hapten of formula I Hapten I

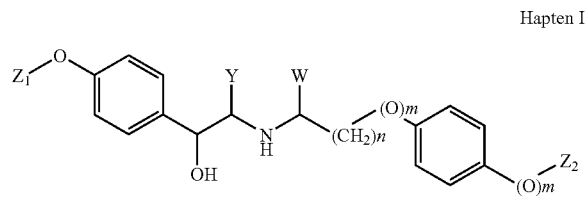

suitable for use in raising an antibody capable of binding with at least one structural epitope of a phenethanolamine such as, but not limited to, ractopamine, isoxsuprine or ritodrine, the method comprising the step of reacting a phenethanolamine derivative of the formula D, in which $Z_1$ is a crosslinker, with a phenylalkylcarbonyl derivative of the formula E, in which $Z_2$ is H; Y is independently H or $CH_3$; W is independently H or $CH_3$; n is independently 1 or 2; and m is independently 0 or 1

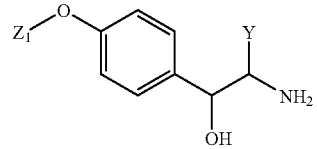

D

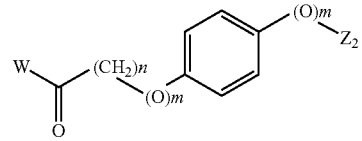

E

Preferably, the phenethanolamine derivative of the formula D is prepared by reacting octopamine hydrochloride with $Z_1X_1$, in which $X_1$ is a halide, preferably a bromide. More preferably, the amine group of the octapamine hydrochloride is temporarily protected with BOC, by reacting the octapamine hydrochloride with di-tert-butyldicarbonate before reacting the BOC-protected octapamine hydrochloride with the $Z_1X_1$, the BOC group being subsequently removed.

In a further aspect, the invention provides a method of preparing a hapten of formula II Hapten II

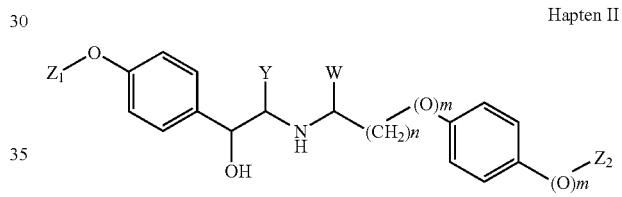

suitable for use in raising an antibody capable of binding with at least one structural epitope of a phenethanolamine such as, but not limited to, ractopamine, isoxsuprine or ritodrine, the method comprising the step of reacting a phenethanolamine derivative of the formula D, in which $Z_1$ is H, with a phenylalkylcarbonyl derivative of the formula E, in which $Z_2$ is a crosslinker; Y is independently H or $CH_3$; W is independently H or $CH_3$; n is independently 1 or 2; and m is independently 0 or 1

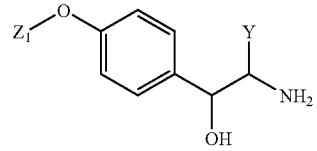

D

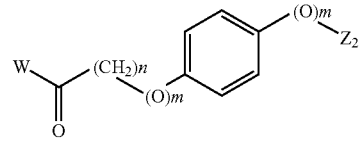

E

Preferably, the phenylalkylcarbonyl derivative of the formula E is prepared by reacting 4-(4-hydroxyphenyl)-2-butanone with $Z_2X_1$, in which $X_1$ is a halide, preferably a bromide.

Preferably, the crosslinker is —R—X$_2$. Preferably, R is a bivalent link and X$_2$ is a heterofunctional group. By "heterofunctional" is meant a functional group containing at least one hetero-atom that is able to link the R of the crosslinker with either antigenicity-conferring carrier materials, to form immunogens or, alternatively, detectable labelling agents, to form conjugates. More preferably, the X$_2$ heterofunctional group is capable of reacting with either antigenicity-conferring carrier materials, to form immunogens or, alternatively, detectable labelling agents, to form conjugates.

Most preferably, R is selected from the group comprising a substituted or unsubstituted, straight or branched chain, saturated or unsaturated alkylene group and a substituted or unsubstituted arylene group such as a benzylene group and X$_2$ is selected from the group comprising a carboxylic acid or an ester thereof; an amine; a maleimide, a halocarboxylic acid or an ester thereof, an aldehyde, a dithiopyridyl group, a vinylsulphone group, and a thiocarboxylic acid or an ester thereof. More preferably, R is a C$_{1-5}$, most preferably a C$_{1-3}$, substituted or unsubstituted, straight chain, saturated alkylene group. Advantageously, X$_2$ is selected from a carboxylic acid or an ester thereof, a thiocarboxylic acid or an ester thereof, a dithiopyridyl, a maleimide, or an aldehyde group. Most advantageously, X$_2$ is a carboxyl group (COOH) or a thioacetyl (SCOCH$_3$) group.

The resulting haptens are deliberately derivatised at a single phenolic hydroxyl group of phenethanolamines such as, but not limited to, ractopamine, isoxsuprine and ritodrine.

The resulting haptens are employed in the preparation of immunogens by coupling them to modified or non-modified antigenicity-conferring carrier materials to provide immunogens for antibody production and conjugates (tracers) that have excellent sensitivity and specificity for the detection or determination of phenethanolamines such as, but not limited to, ractopamine, isoxsuprine and ritodrine.

The invention therefore provides an immunogen comprising a hapten prepared in accordance with the present invention, coupled to an antigenicity-conferring carrier material. Preferably, the carrier material is a protein, a protein fragment, a synthetic polypeptide or a semi-synthetic polypeptide.

The immunogens obtained are then administered to mammalian hosts to elicit production of specific antibodies, preferably polyclonal antibodies, which are then used to develop competitive immunoassays for phenethanolamines such as, but not limited to, ractopamine, isoxsuprine and ritodrine, employing haptens conjugated to labelling agents as conjugates or detection reagents.

In a still further aspect, the present invention concerns antibodies raised against the immunogens of the present invention, the antibodies being capable of binding with at least one structural epitope of phenethanolamines such as, but not limited to, ractopamine, isoxsuprine and ritodrine. Preferably, the antibodies are fixed on a backing substrate. More preferably, the antibodies show a cross reactivity, when compared to 100% for ractopamine, isoxsuprine and ritodrine, of less than 5% for dobutamine. More preferably, the antibodies show a cross reactivity, when compared to 100% for ractopamine and isoxsuprine of less than 2.5%, more preferably less than 1.5%, for dobutamine. Separately or additionally, the antibodies raised to ractopamine show a cross reactivity, when compared to 100% for ractopamine, of less than 0.75%, preferably less than 0.6%, for ritodrine and isoxsuprine. Separately or additionally, the antibodies raised to isoxsuprine show a cross reactivity, when compared to 100% for isoxsuprine, of less than 0.75%, preferably less than 0.6%, more preferably less than 0.25%, for each of ritodrine and ractopamine. Separately or additionally, the antibodies raised to ritodrine show a cross reactivity, when compared to 100% for ritodrine, of less than 0.75%, preferably less than 0.6%, for ractopamine.

In a still further aspect, the present invention comprises conjugates comprising the haptens prepared in accordance with the method of the present invention covalently bonded to a detectable labelling agent. Preferably, the labelling agent is selected from an enzyme, a luminescent substance, a radioactive substance, or a mixture thereof. More preferably, the labelling agent is an enzyme, preferably a peroxidase, most preferably horseradish peroxidase (HRP). Alternatively, or additionally, the luminescent substance may be a bioluminescent, chemiluminescent or fluorescent material.

The invention further provides a process of preparing the antibodies, the process comprising the steps of immunising an animal, preferably a vertebrate animal, most preferably a mammalian animal, by repeated administration of an immunogen prepared in accordance with the present invention, and collecting the resulting serum from the immunised animal. Preferably, the process further comprises fixing said serum antibodies to a backing substrate, preferably a solid support, most preferably a polystyrene solid support. Preferably, the antibodies are polyclonal. Alternatively, the antibodies are monoclonal.

In a still further aspect, the present invention comprises a method for detecting or determining phenethanolamines such as, but not limited to, ractopamine, isoxsuprine and ritodrine in a sample, the method comprising contacting the sample with at least one conjugate of the present invention, and with at least one antibody of the present invention; detecting or determining bound conjugate; and deducing from a calibration curve the presence of, or the amount of, the phenethanolamine in the sample.

In a further aspect, the invention includes a kit for detecting or determining phenethanolamines such as, but not limited to, ractopamine, isoxsuprine or ritodrine, the kit including at least one conjugate prepared in accordance with the present invention; and at least one antibody prepared in accordance with the present invention. The kit may optionally include instructions for the use of said conjugates and said antibodies for detecting or determining phenethanolamines such as, but not limited to, ractopamine, isoxsuprine or ritodrine in a sample.

The methods and kits using antibodies and conjugates raised to ractopamine of the present invention show an IC$_{50}$ of less than 2.5, preferably less than 1.5, more preferably less than 0.75, most preferably less than 0.25, ng/ml for ractopamine. The methods and kits, using antibodies and conjugates raised to isoxsuprine, show an IC$_{50}$ of less than 2.5, preferably less than 1.5, more preferably less than 0.75, more preferably less than 0.25, ng/ml for isoxsuprine. The methods and kits, using antibodies and conjugates raised to ritodrine, show an IC$_{50}$ of less than 250, preferably less than 150, ng/ml for ritodrine Preferably, the antibodies are provided, fixed onto a backing substrate, the backing substrate preferably being a solid support which is, for example, a polystyrene solid support. This can take the form of a microtitre plate or, alternatively, a Biochip (Trade Mark) such as is disclosed in U.S. Pat. No. 6,498,010. Phenethanolamines such as, but not limited to, ractopamine, isoxsuprine or ritodrine, if present in the standard and sample, compete with conjugates comprising haptens covalently bonded to a detectable labelling agent such as, but not restricted to, horseradish peroxidase, for the limited number of antibody sites on the backing substrate. After incubation at room temperature to allow a competition reaction to take place, the backing substrate is then washed to remove excess reagents. If the labelling agent is horseradish peroxidase, its substrate is then added and an incubation period follows to allow maximum signal development. In an ELISA format, the colour development is then stopped by the addition of acid and this produces a colour change from blue to yellow. The absorbance is read at 450 nm. A standard curve is then constructed to determine the concentration of the phenethanolamine such as, but not limited to, ractopamine, isoxsuprine or ritodrine in the sample and the standard. Alternatively, in the Biochip format, the signal generated is typically chemiluminescent and the light level generated is quantified by a charge coupled device (CCD) camera to determine the concentration of the phenethanolamines such as, but not limited to, ractopamine, isoxsuprine and ritodrine in the sample or standard.

Preferably, the sample is a solution, such as a biological fluid. More preferably, the sample is serum or urine.

Urine samples may be analysed following a dilution method. However, if the urine appears dirty or a lower detection limit is required, an appropriate extraction method should be used. Simple dilution involves centrifuging the urine sample at, for example, 13000 rpm for 10 minutes and then diluting the centrifuged urine ten fold in diluted diluent/wash buffer, following which the sample can be applied to the backing substrate.

Intra-assay precision of the ELISA kit was determined employing negative urine samples spiked with 1 ng/ml and 5 ng/ml. The results were 5.95 and 6.62% CV, respectively. Inter-assay precision of the ELISA kit for the same spiked urine samples was also determined and the results were 11.83 and 5.90% CV, respectively.

In the method and kit of the present invention, it is preferred that the respective crosslinkers (of the immunogen and the conjugate) are different.

In a further aspect, the present invention involves the use of the conjugates of the present invention, or a mixture thereof, with the antibodies of the present invention, or a mixture thereof, to detect or determine phenethanolamines such as, but not limited to, ractopamine, isoxsuprine or ritodrine in samples such as tissues or biological fluids.

Preparation of Haptens

Figure 3:
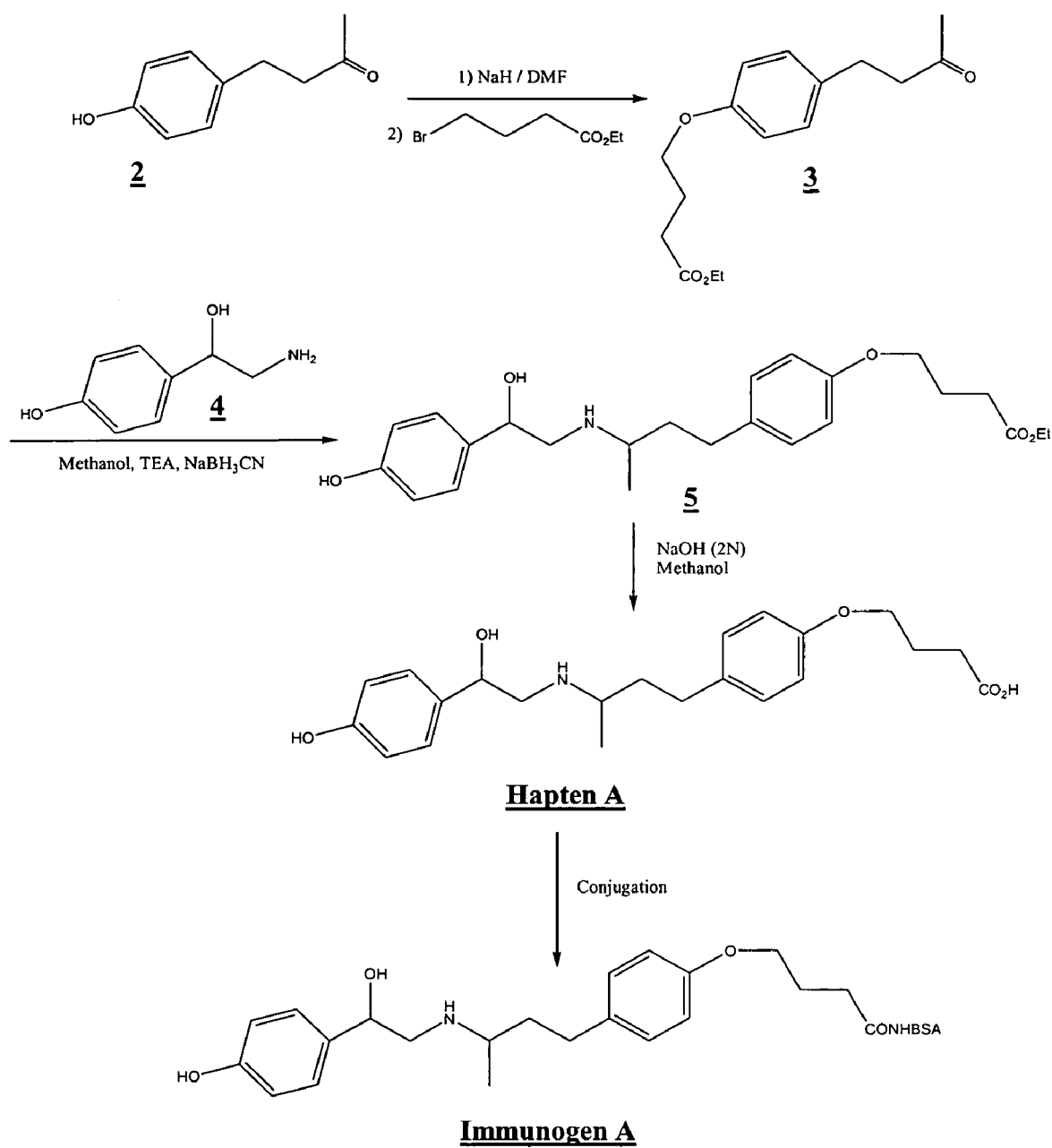
FIG. 3 shows the reaction scheme for the preparation of Hapten/Immunogen A.

The hapten [10-O-(carboxypropyl)]ractopamine ether (Hapten A—derivatised at position 10) was prepared in three steps according to FIG. 3 of the accompanying drawings, from 4-(4-hydroxyphenyl)-2-butanone, 2. The reaction of 4-(4-hydroxyphenyl)-2-butanone, 2 with ethyl 4-bromobutyrate in dimethylformamide (DMF) in the presence of sodium hydride (NaH), gives ethyl 4-[4-(3-oxobutyl)phenoxy]butanoate 3. The ketoester, 3, obtained was reacted with octopamine hydrochloride, 4, in methanol in the presence of triethylamine (TEA) and sodium cyanoborohydride (Na BH$_3$CN) to give 10-O-[3-(ethoxycarbonyl)propyl]ractopamine ether 5, in moderate yields. The hapten A was obtained after saponification of the ester, 5, with sodium hydroxide (NaOH) (2N) in methanol.

Figure 4:
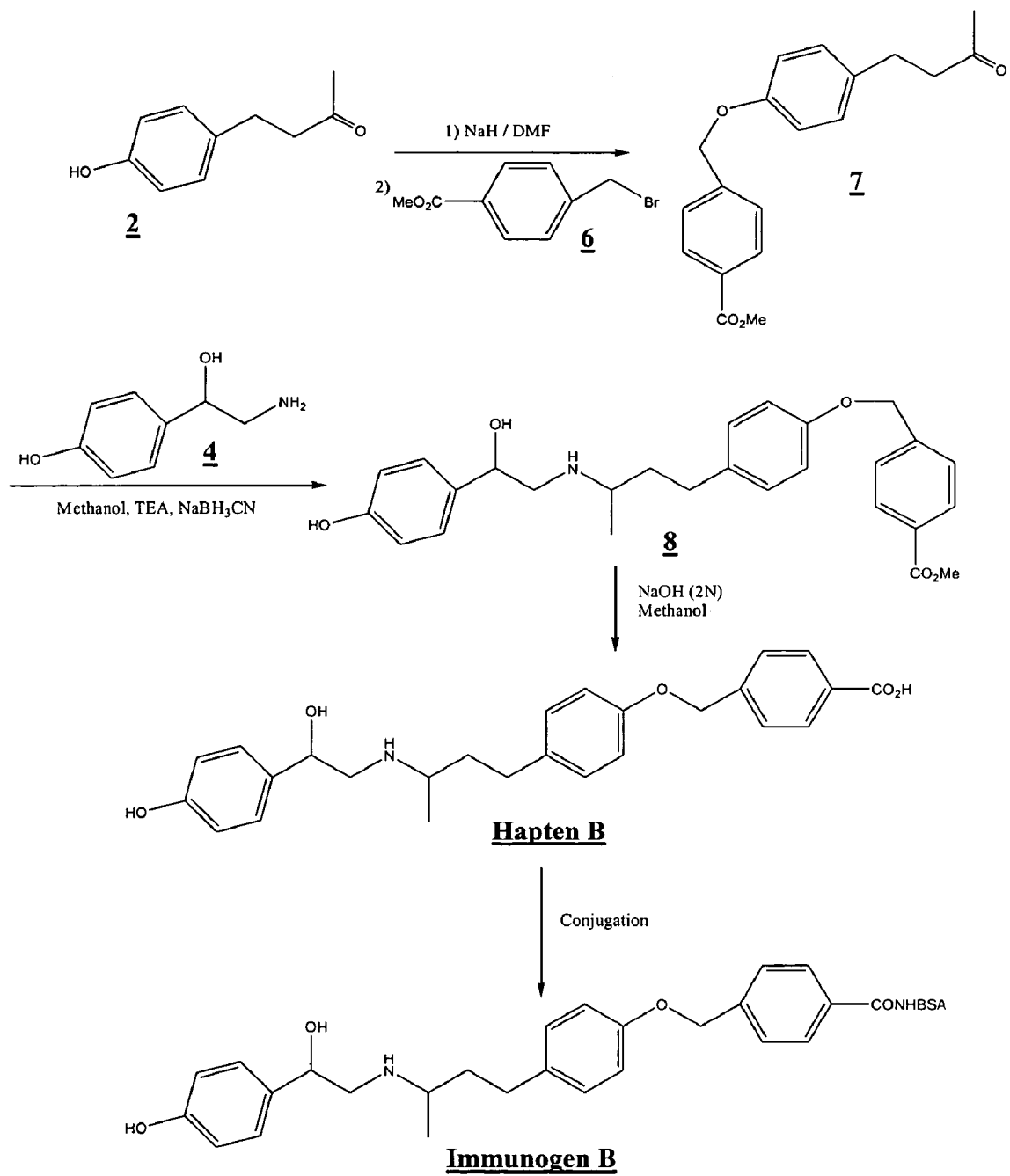
FIG. 4 shows the reaction scheme for the preparation of Hapten/Immunogen B.

The hapten 10-O-(4-carboxybenzyl)ractopamine ether (hapten B—derivatised at position 10) was prepared by the same method as hapten A in three steps according to FIG. 4 of the accompanying drawings, from 4-(4-hydroxyphenyl)-2-butanone, 2. The reaction of 2 with methyl 4-(bromomethyl)benzoate, 6, in DMF in the presence of NaH, gives methyl 4-[4-(3-oxobutyl)phenoxymethyl]benzoate, 7. The condensation of the keto ester, 7 with octopamine hydrochloride, 4 in methanol in the presence of triethylamine (TEA) and sodium cyanoborohydride gives the ester 8. The hapten B was obtained after saponification of the ester 8 with sodium hydroxide (2N) in methanol.

Figure 5:
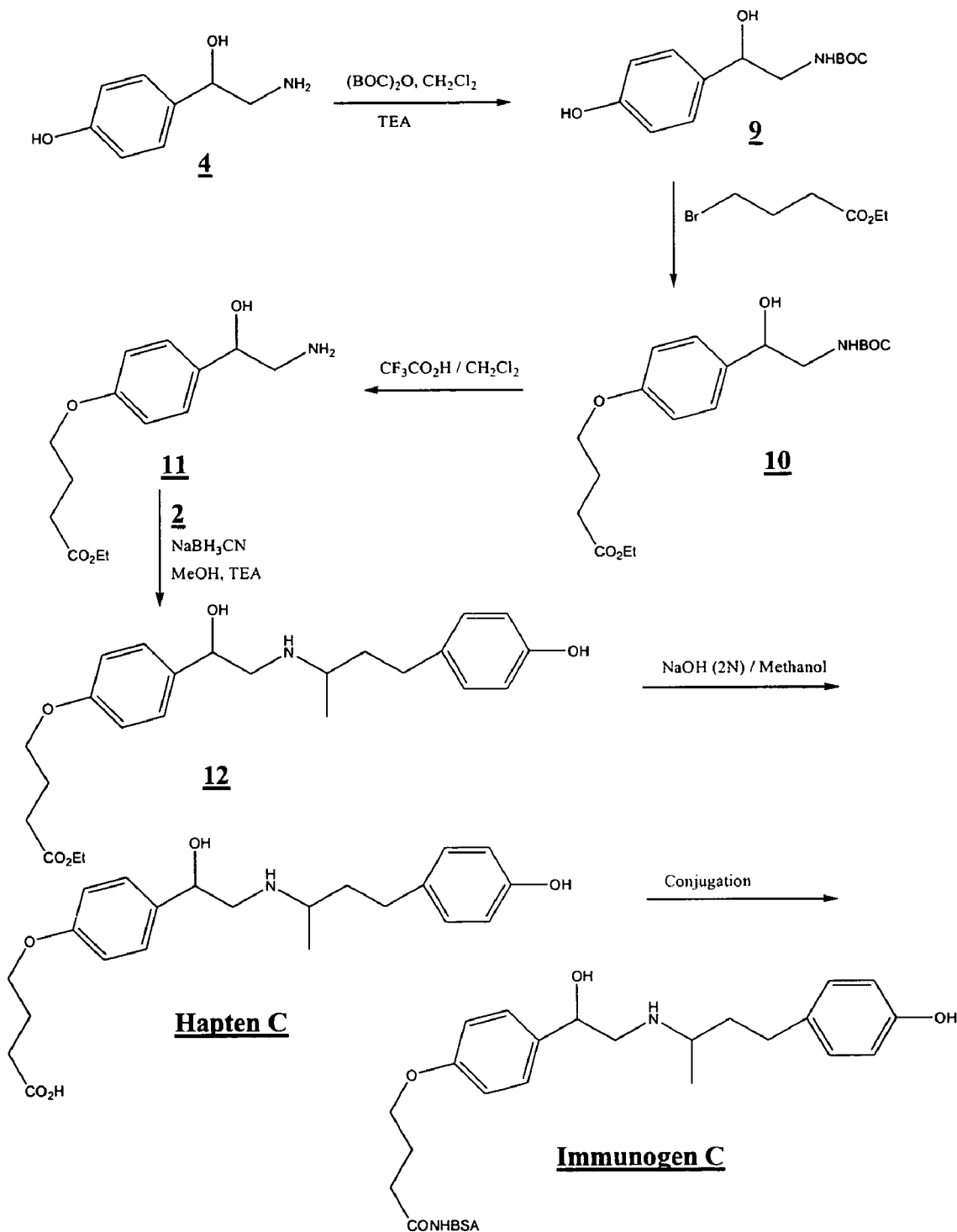
FIG. 5 shows the reaction scheme for the preparation of Hapten/Immunogen C.

The hapten 10'-O-(3-carboxypropyl)ractopamine ether (Hapten C—derivatised at position 10') was prepared in six steps, according to FIG. 5 of the accompanying drawings, from octopamine hydrochloride 4. The N-BOC protected octopamine, 9 was obtained by reaction of 4 with di-tert-butyldicarbonate (BOC$_2$O) in methanol in the presence of TEA. The reaction of N-BOC octopamine, 9 with ethyl-4-bromobutyrate in acetonitrile in the presence of potassium carbonate (K$_2$CO$_3$) gives the ester 10 in good yield. The treatment of 10 with trifluoroacetic acid in dichloromethane gives ethyl 4-[4-(2-amino-1-hydroxyethyl)phenoxy]butanoate, 11. The condensation of octopamine derivative 11 with 4-(4-hydroxyphenyl)-2-butanone 2 in methanol in the presence of TEA and sodium cyanoborohydride (NaBH$_3$CN) gives 10'-O-[3-(ethoxycarbonyl)propyl]ractopamine ether 12. The hapten 10'-O-(3-carboxypropyl)ractopamine ether, Hapten C, was obtained after saponification of the ester 12 by using sodium hydroxide (2N) in methanol.

Figure 6:
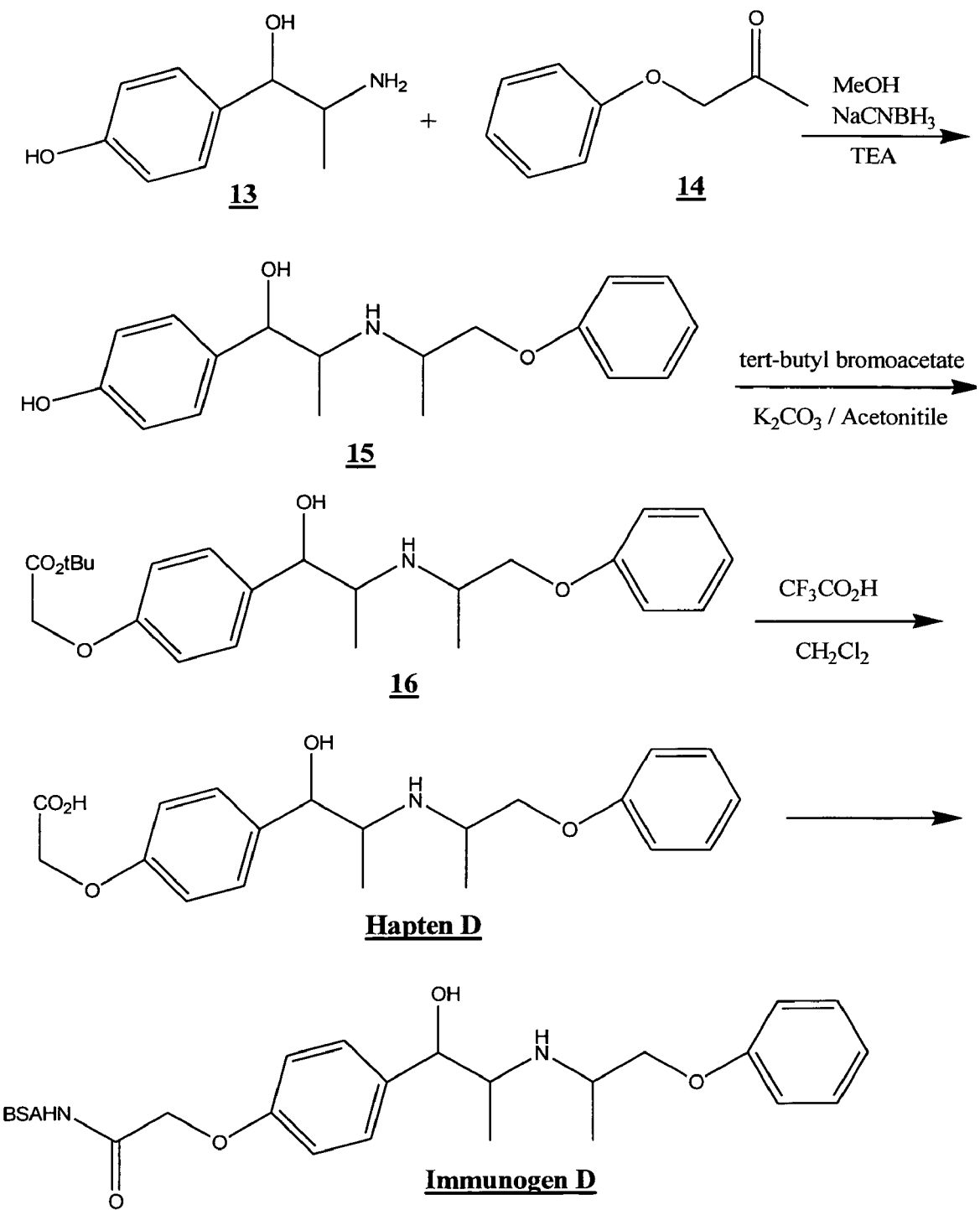
FIG. 6 shows the reaction scheme for the preparation of Hapten/Immunogen D.

The hapten p-(carboxymethyl)isoxsuprine (Hapten D) was prepared in four steps according to FIG. 6 of the accompanying drawings, from α-(1-aminoethyl)-4-hydroxybenzyl alcohol hydrochloride 13. The isoxsuprine 15 was obtained by reaction of 13 with phenoxy-1-propanone 14 in methanol in the presence of sodium cyanoborohydride and triethyl amine. The ester 16 was obtained by selective alkylation of isoxsuprine 15 with t-butyl bromoacetate in acetonitrile in the presence of potassium carbonate. The treatment of the ester 16 with trifluoroacetic acid in dichloromethane gave the p-(carboxymethyl)isoxsuprine, Hapten D.

Figure 7:
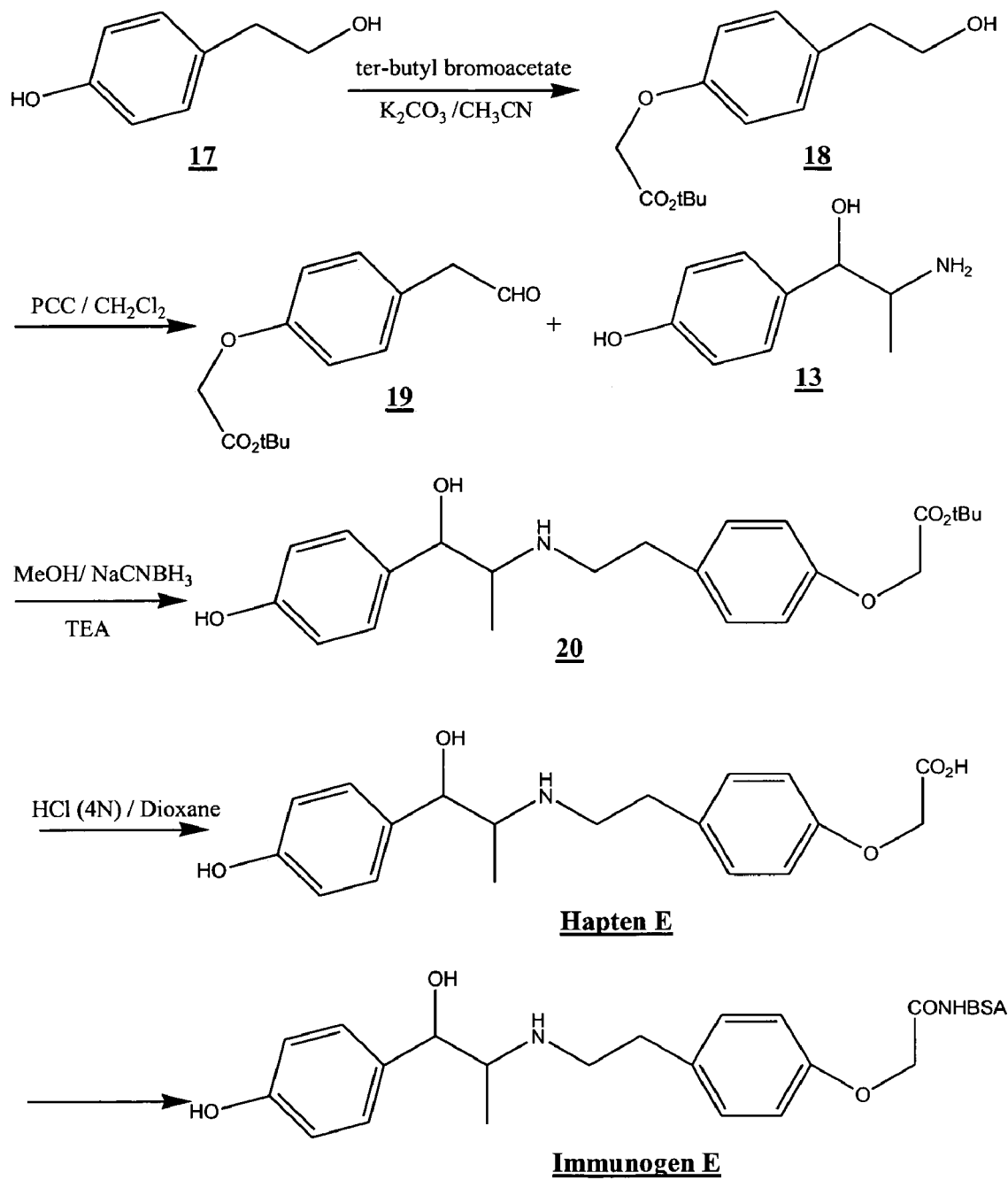
FIG. 7 shows the reaction scheme for the preparation of Hapten/Immunogen E.

The hapten p-(carboxymethyl)ritodrine (Hapten E) was prepared in four steps according to FIG. 7 of the accompanying drawings, from 2-(4-hydroxyphenyl)ethanol 17. The reaction of 17 with t-butyl bromoacetate in acetonitrile in the presence of potassium carbonate at 60° C. gives 2-[4-(t-butoxycarbonylmethoxy)phenyl]ethanol 18. The oxidation of the alcohol 18 with pyridinium chlorochromate (pcc) in dichloromethane gives the 2-[4-(t-butoxycarbonylmethoxy)phenyl]ethanal 19. The ester 20, obtained by condensation of the aldehyde 19 with α-(1-aminoethyl)-4-hydroxybenzyl alcohol hydrochloride 13 in methanol in the presence of sodium cyanoborohydride and triethylamine. Deprotection of the t-butyl protecting group of the ester 20 with 4 M HCl in dioxane at room temperature gave Hapten E in moderate yield.

Preparation of Immunogens and Conjugates

Although the haptens of the present invention provide defined structural epitopes, they are not in themselves immunogenic and therefore need to be conjugated to carrier materials, which will elicit an immunogenic response when administered to a host animal. Appropriate carrier materials commonly contain poly(amino acid) segments and include polypeptides, proteins and glycoproteins. Illustrative examples of useful carrier materials are bovine serum albumin (BSA), egg ovalbumin, bovine gamma globulin, thyroxine binding globulin, keyhole limpet haemocyanin (KLH) etc. Alternatively, synthetic poly(amino acids) having a sufficient number of available amino groups, such as lysine, may be employed, as may other synthetic or natural polymeric materials bearing reactive functional groups. In particular, carbohydrates, yeasts or polysaccharides may be conjugated to the hapten to produce an immunogen.

Each hapten prepared in accordance with the present invention can also be coupled to a detectable labelling agent such as an enzyme (for example, horseradish peroxidase), a substance having luminescent, chemiluminescent or fluorescent properties or a radioactive label for the preparation of conjugates (or detection reagents) for use in the immunoassays. The fluorescent substance may be, for example, a monovalent residue of fluorescein or a derivative thereof.

In order to confirm that adequate conjugation of hapten to carrier material has been achieved, prior to immunisation, each immunogen is evaluated using matrix-assisted UV laser desorption/ionisation time-of-flight mass spectroscopy (MALDI-TOF MS). Each of the immunogens of the present invention is suitable for immunisation, in order to produce antibodies for the detection of phenethanolamines such as, but not limited to, ractopamine, isoxsuprine and ritodrine.

General Procedure for MALDI-TOF Analysis of Immunogens

MALDI-TOF mass spectrometry was performed using a Voyager STR Biospectrometry Research Station laser-desorption mass spectrometer coupled with delayed extraction. An aliquot of each sample to be analysed was diluted in 0.1% aqueous trifluoroacetic acid (TFA) to create 1 mg/ml sample solutions. Aliquots (1 μl) were analysed using a matrix of Sinapinic acid and bovine serum albumin (Fluka) was used as an external calibrant.

Preparation of Antisera

In order to generate polyclonal antisera, each immunogen of the present invention is mixed with Freund's Adjuvant and the mixture is injected into a host animal, such as rabbit, sheep, mouse, guinea pig or horse. Further injections (boosts) are made and serum is sampled for evaluation of the antibody titre. When the optimal titre has been attained, the host animal is bled to yield a suitable volume of specific antiserum. The degree of antibody purification required depends on the intended application. For many purposes, there is no requirement for purification, however, in other cases, such as where the antibody is to be immobilised on a solid support, purification steps can be taken to remove undesired material and eliminate non-specific binding.

The specific antibodies prepared in this invention are useful as reagents in immunoassays for the detection or determination of phenethanolamines such as, but not limited to, ractopamine, isoxsuprine and ritodrine in biological fluids.

EXAMPLES

Example 1

Preparation of Ethyl 4-[4-(3-oxobutyl)phenoxy]butanoate 3

To a suspension of sodium hydride (60% dispersion in mineral oil) (7.3 g, 0.183 mole) in anhydrous DMF (100 ml) under nitrogen atmosphere was added drop-wise 4-(4-hydroxyphenyl)-2-butanone 2 (20.0 g, 0.122 mole) in anhydrous DMF (100 ml) and the mixture was then stirred at room temperature for one hour. To this mixture was added drop-wise ethyl 4-bromobutyrate (28.5 g, 0.146 mole) in anhydrous DMF (50 ml), and the mixture was then stirred at 60° C. overnight. The DMF was removed under reduced pressure and water (200 ml) was then added to the residue and extracted with ethyl acetate (3×200 ml). The combined organic phases were washed with brine (1×200 ml), dried over magnesium sulfate, filtered and evaporated to dryness. The residue obtained was purified by flash chromatography on silica gel using 20% ethyl acetate in hexane as eluant to give 3 as a colourless oil (16.95 g, 50%).

I.R (Film): 1732; 1720; 1612.5; 1512.9; 1245.1 and 1178.

Example 2

Preparation of 10-O-[3-(Ethoxycarbonyl)propyl]ractopamine ether 5

To a solution of 3 (16.95 g, 0.061 mole) and octopamine.HCl (11.57 g, 0.061 mole) in methanol (300 ml) was added TEA (12.35 g, 0.122 mole) and sodium cyanoborohydride (3.83 g, 0.061 mole). The mixture was stirred at 50° C. overnight. Solvents were removed in vacuo. To the residue were added HCl (1N) (150 ml) and water (150 ml) and washed with ether (1×300 ml). The aqueous phase was adjusted to pH12–13 using sodium hydroxide (6N) and extracted with ethyl acetate (3×250 ml). The organic layers were combined, dried over magnesium sulfate, filtered and evaporated to dryness. The crude product was purified by flash chromatography on silica gel using 5–10% methanol in chloroform to give the title compound 5 (7 g, 28%) as a white solid.

I.R (KBr): 3506; 3301.2; 1735.8; 1613.2; 1512.6; 1374.03; 1244.1; 1176.9 and 1046.5.

Example 3

Preparation of 10-O-(3-Carboxypropyl)ractopamine ether (Hapten A)

To a solution of the ester 5 (7 g, 0.169 mole) in methanol (90 ml) was added sodium hydroxide (2N) (30 ml). The mixture was stirred at room temperature for 16 hours. The solvents were removed in vacuo and water (50 ml) was added. The pH of the solution was adjusted to 3–4 by addition of HCl (1N) and the resultant precipitate obtained was collected by filtration and dried in a desiccator over $P_2O_5$. The hapten A was obtained as a white solid (5.64 g, 86%).

Example 4

Preparation of Methyl 4-[4-(3-oxobutyl)phenoxymethyl]benzoate 7

The ester 7 was obtained by using the same method as described in Example 1 using 4-(4-hydroxyphenyl)-2-butanone, 2 (20 g, 0.122 mole), sodium hydride (7.3 g, 0.183 mole) and methyl 4-(bromomethyl) benzoate (33.44 g, 0.146 mole) 6. The title compound 7 was obtained as a clear oil (23.2 g, 61%).

Example 5

Preparation of 10-O-[4-(Methoxycarbonyl)benzyl]ractopamine ether 8

The ester 8 was obtained by using the same method as described in Example 2 for the preparation of 5, using the ester 7 (10.3 g, 0.33 mole), octopamine hydrochloride 4 (6.26 g, 0.33 mole), triethylamine (6.68 g, 0.066 mole) and sodium cyanoborohydride (2.07 g, 0.33 mole). The ester 8 was obtained in moderate yield (7 g, 50%).

I.R (KBr ): 3171.4; 3025.6; 2942.3; 2850.69; 1717.08; 1612.84; 1595.68; 1511.9; 1281.1; 1250.1 and 1107.

Example 6

Preparation of 10-O-(4-Carboxybenzyl)ractopamine ether (hapten B)

The hapten B was obtained in 77% yield as a white solid using the same method as described for the preparation of hapten A (cf.Example 3).

I.R (KBr): 3118.8; 3034.2; 1700.7; 1613.6; 1515.56; NMR 13C (CD3OD): 169.6; 158.6; 158.5; 144.2; 134.2; 132.9; 131.3(2C); 130.9(2C); 130.5; 128.4(2C); 128.1(2C); 116.4(2C); 116.1(2C); 70.3; 70.1; 52.3; 52.25; 35.4; 31.8 and 16.5.

Example 7

Preparation of N-[2-Hydroxy-2-(4-hydroxyphenyl)ethyl]t-butylcarboxamide 9

To a solution of octopamine hydrochloride 4 (18.96 g, 0.1 mole) in methanol (200 ml) was added TEA (20.24 g, 0.2 mole) and di-tert-butyldicarbonate (26.19 g, 0.12 mole). The mixture was stirred at room temperature overnight. Solvents were removed in vacuo and the crude residue obtained was purified by flash chromatography on silica gel using ethyl acetate as eluant to give N-BOC octopamine 9 (23.2 g, 80%) as a white solid.

Example 8

Preparation of Ethyl 4-{4-[2-(t-butylcarboxamido)-1-hydroxyethyl]phenoxy}butanoate 10

To a solution of N-BOC octopamine 9 (23.2 g, 0.08 mole) in acetonitrile (400 ml) was added potassium carbonate (44.29 g, 0.32 mole) and ethyl bromobutyrate (23.41 g, 0.12 mole). The mixture was stirred and heated at reflux overnight. The solution was then allowed to cool to room temperature, filtered and concentrated to dryness. The residue obtained was purified by flash chromatography on silica gel using 50% ethyl acetate in hexane as eluant to give the title compound 10 (24.53 g, 78%) as a clear oil.

I.R (Film): 3434.2; 2979.7; 2934.5; 1731.3(broad); 1611.9; 1512.5; 1367.5; 1247.2 and 1172.8.

Example 9

Preparation of Ethyl 4-[4-(2-amino-1-hydroxyethyl)phenoxy]butanoate trifluoroacetic acid salt 11.

To a solution of ethyl 4-(carboxypropyl)-N-BOC octopamine 10 (14.26 g, 0.0363 mole) in dichloromethane (80 ml) was added trifluoroacetic acid (40 ml) and the mixture was stirred at room temperature for 1 hour. The solvents were removed in vacuo and the crude product obtained was purified by flash chromatography on silica gel using (10% methanol in chloroform) to give the title compound 11 (12.2 g, 83%) as a viscous oil.

Example 10

Preparation of 10'-O-[3-(Ethoxycarbonyl)propyl]ractopamine ether 12

The ester 12 was prepared by condensation of compound 11 (21.89 g, 0.0574 mole) with 4-(4-hydroxyphenyl)-2-butanone, 2 (9.43 g, 0.0574 mole) using the same method as described for the preparation of 5 and 8. The title compound 12 (10 g, 42%) was obtained as a yellow oil.

I. R(Film): 3297.7(broad); 2936.7; 1732.1; 1612.07; 1514.5; 1446.4; 1375.5; 1174.3 and 1029.7

Example 11

Preparation of 10'-O-(3-Carboxypropyl)ractopamine ether Hapten C

The hapten C was obtained after saponification of the ester 12, using the same method as described for the preparation of haptens A and B, as a white solid (6.2 g, 66%).

NMR 13C (CD30D): 177.17; 160.46; 156.9; 134.3; 132.4; 130.4(2C); 128.4(2C); 116.4(2C); 115.7(2C); 70.0; 68.1, 55.4; 52.2; 35.6; 31.7; 31.5; 25.8 and 16.5

Example 12

Preparation of Isoxsuprine 15

To a solution of α-(1-aminoethyl)-4-hydroxybenzyl alcohol 13 (10.0 g, 0.049 mole) and phenoxy-2-propanone 14 (7.4 g, 0.049 mole) in methanol (200 ml) was added TEA (10.5 g, 0.102 mole). The mixture was stirred at room temperature overnight. Solvents were removed in vacuo. To the residue were added HCl (1N) (100 ml) and water (100 ml) and this was extracted with ethyl acetate (1×200 ml). The aqueous phase was made basic (pH 12–13) using sodium hydroxide (6N) and extracted with ethyl acetate (3×200 ml). The organic extracts were combined and washed with brine (1×200 ml), dried over sodium sulfate, filtered and evaporated to dryness. The crude product was purified by flash chromatography on silica gel using 10% methanol in chloroform to give isoxsuprine 15 (8 g, 54%) as a white solid, m.p. 102–104° C.

Example 13

Preparation of 10'-O-(4-tert-Butoxycarbonylmethyl)isoxsuprine ether 16

Isoxsuprine, 15 (3.1 g, 10.3 mMoles) was dissolved in acetonitrile (100 ml). To this solution was added potassium carbonate (4.48 g, 32.4 mMoles) and tert-butyl bromoacetate (3.16 g, 16.2 mMoles) and the mixture heated at reflux overnight. The mixture was allowed to cool, filtered and the filtrate concentrated in vacuo. The crude product so obtained was purified by flash chromatography on silica gel using 5% methanol in chloroform to give 16 (2.27 g, 52%) as a colourless oil. NMR $^{13}$C (CDCl$_3$): 168.1, 158.7, 157.0, 134.5, 128.5, 127.3, 120.9, 114.5, 83.3, 73.7, 71.9, 65.9, 56.0, 49.6, 28.0, 18.3 and 15.2.

Example 14

Preparation of 10'-O-(4-Carboxymethyl)isoxsuprine ether, Hapten D

To a solution of 10'-O-(4-tert-butoxycarbonylmethyl) isoxsuprine ether 16 (2.08 g, 4.8 mMoles) in dichloromethane (25 ml) was added trifluoroacetic acid (10 ml) and the mixture was stirred at room temperature for two hours. The solvent was removed in vacuo and the crude product obtained was purified by flash chromatography on silica gel using 10% methanol in chloroform to give the Hapten D as a TFA salt (1.5 g, 66%).

Example 15

Preparation of tert-Butyl 4-[2-hydroxyethyl]phenoxyacetate 18

To a solution of 2-(4-hydroxyphenyl)ethanol 17 (27.6 g, 0.2 mole) in acetonitrile (300 ml) was added potassium carbonate (110.5 g, 0.8 mole) and tert-butyl bromo acetate (46.8 g, 0.24 mole) and the mixture was stirred and heated at reflux for two hours. The mixture was allowed to cool, filtered and the filtrate concentrated in vacuo. The crude product obtained was purified by chromatography on silica gel by using 30% ethyl acetate in hexane to tert-butyl 4-[2-hydroxyethyl]phenoxyacetate 18 (39.8 g, 83%) as a clear oil.

Example 16

Preparation of tert-Butyl 4-[formylmethyl]phenoxyacetate 19

To a solution of 18 (20.0 g, 0.083 mole) in anhydrous dichloromethane (200 ml) was added pyridinium chlorochromate (PCC) (44.7 g, 0.207 mole) and the mixture was stirred at room temperature for two hours. Ether (500 ml) was then added to quench the reaction and the mixture was then filtered through C elite. (Trade Mark) Evaporation of the solvents in vacuo afforded the crude product which was purified by flash chromatography on silica gel using 20% ethyl acetate in hexane to give 19 (16.6 g, 80%) as a yellow oil.

Example 17

Preparation of t-Butyl 4-[-2-(beta-hydroxy-alpha-methyl-4-hydroxyphenethylamino)ethyl]phenoxyacetate, 20

The ester 20 was prepared by condensation of tert-butyl 4-[formylmethyl]phenoxyacetate (10.0 g, 0.04 mole) with α-(1-aminoethyl)-4-hydroxybenzyl alcohol 13 (8.2 g, 0.04 mole) using the same method as described for the preparation of 5, 8, and 16. The ester 20 (8.18 g, 51%) was obtained as a yellow oil.

Example 18

Preparation of 4-[-2- (beta-hydroxy-alpha-methyl-4-hydroxyphenethylamino)ethyl]phenoxyethanoic acid, Hapten E To a solution of tert-butyl ester 20 (3.7 g, 0.92 mMole) in 25 ml of anhydrous dioxane was added hydrochloric acid solution (4M) in dioxane (25 ml) and the mixture was stirred overnight at room temperature. Evaporation of the solvents in vacuo afforded the crude product which was purified by flash chromatography on silica gel using 10% methanol in chloroform to give the hapten E HCl salt.(1.2 g, 34.2%) as a foamy solid.

NMR$^{13}$C (CD$_3$OD): 171.4, 159.6, 158.6, 132.6 (2), 131.6 (2), 130.8 (2), 128.3 (2), 116.6, 116.1, 84.8, 66.8, 59.8, 52.7, 32.6 and 19.4.

Example 19

Conjugation of Haptens A, B, C, D and E to BSA (Preparation of Immunogens A, B, C, D and E)

To a solution of hapten A, B, C, D or E (58 mg, 0.15 mmole) in DMF(1 ml) was added N,N-dicyclohexylcarbodiimide (DCC) (34 mg, 0.165 mmole) and N-hydroxysuccinimide (19 mg, 0.165 mmole) and the mixture stirred at room temperature overnight. The dicyclohexylurea formed was removed by filtration and the filtrate added drop-wise to a solution of BSA (200 mg) in 0.1M sodium hydrogen carbonate, pH8.5 (12 ml). The mixture was stirred at room temperature overnight. The solution was dialysed against 50 mM phosphate buffer, pH7.2 (3 changes) for 24 hours at 4° C. and then freeze-dried.

MALDI results showed 17 molecules of hapten A, 5.8 molecules of hapten B, 10.7 molecules of hapten C, 12.4 molecules of Hapten D and 6.2 molecules for hapten E had been conjugated to 1 molecule of BSA.

Example 20

General Method for the Conjugation of Haptens A, B, C, D and E to HRP (Horseradish Peroxidase)

EDC.HCl (10 mg) was dissolved in water (0.5 ml) and immediately added to a solution of Hapten (A or B or C or D or E) (2 mg) in DMF (0.2 ml). After mixing, this solution was added drop-wise to a solution of HRP (20 mg) in water (1 ml). Sulfo-NHS (5 mg) was added and the reaction mixture was incubated in the dark at room temperature overnight. Excess hapten was removed by desalting with PD-10 columns (Pharmacia) in series, pre-equilibrated with PBS (phosphate buffered saline) at pH 7.2. The hapten-HRP conjugate was then dialysed overnight against 10 L of PBS pH 7.2 at 4° C.

Example 21

Preparation of Antibodies to Immunogens A and C, Prepared in Example 19

An aqueous solution of each immunogen was formulated with Freund's Complete Adjuvant (FCA) to form an emulsion consisting of 2 mg/ml immunogen in 50% (v/v) FCA. Three sheep were immunised with this emulsion (1° immunisation), 0.25 ml being subcutaneously injected at each of four sites in the flank of each animal. Subsequent immunizations (boosts) contained 1 mg/ml immunogen. All boosts were emulsified in 50% (v/v) Freund's Incomplete Adjuvant (FIA) and were administered in the same manner as the 1° immunisation, at monthly intervals for 1 year. Blood sampling took place 7 to 14 days after each boost. Each sample was processed to produce antiserum, which was further purified by caprylic acid and ammonium sulfate precipitation to yield an immunoglobulin G (IgG) fraction. The IgG fraction was evaluated by competitive ELISA microtiter plate assay, as described in Example 22 below.

Example 22

Development of Competitive ELISAs for Ractopamine a) The wells of an enhanced binding 96 well polystyrene microtiter plate were coated with the IgG fraction of the antiserum raised to immunogen A (hapten A-BSA) (Example 19), diluted in 10 mM Tris, pH8.5 (125 µl/well). The appropriate antibody coating dilution was determined using standard ELISA checkerboard techniques. The plate was incubated for 2 hours at 37° C., washed 4 times with Tris buffered saline containing Tween 20 (TBST) and tapped dry. Standard solutions of ractopamine were prepared in TBST at 0, 0.05, 0.1, 0.5, 1, and 5 ng/ml, and 50 µl of each was added to the appropriate wells. 75 µl of conjugate A (hapten A-HRP) (Example 20), diluted in Tris buffer (pH 7.2) containing EDTA, D-mannitol, sucrose, thimerosal and BSA, was added to each of the wells. The appropriate dilution of conjugate was also determined using standard ELISA checkerboard techniques. The plate was incubated at 37° C. for 2 hours. Excess unbound conjugate was removed by washing 6 times over a 10 minute period with TBST. 125 µl of tetramethylbenzidine (TMB) substrate solution was added to each well of the plate that was then incubated for 15 to 20 minutes in the dark at room temperature. The reaction was terminated by addition of 125 µl 0.2M $H_2SO_4$ to each well. The absorbance was then measured at 450 nm using a microtiter plate reader. The data generated in the assay is presented in Table 1.

b) In a similar manner to that described in Example 15(a), the wells of a 96-well microtiter plate were coated with the IgG fraction of the antiserum raised to immunogen C (hapten C-BSA) (Example 19), standards were applied at 0, 0.025, 0.1, 0.25, 0.5 and 1 ng/ml and conjugate C (hapten C-HRP) (Example 20) was employed as detection reagent. The data generated are presented in Table 1. The same definitions apply for $A_{450}$, B, $B_0$ and $IC_{50}$.

TABLE 1

Data generated from competitive microtiter plate assays for ractopamine, employing antisera generated to immunogen A (hapten A-BSA) (Example 19) and immunogen C (hapten C-BSA) (Example 19).

| Example 22 a) | | | Example 22 b) | | |
|---|---|---|---|---|---|
| Ractopamine Concentration ng/ml | $A_{450}$ | % $B/B_0$ | Ractopamine Concentration ng/ml | $A_{450}$ | % $B/B_0$ |
| 0 | 2.385 | 100 | 0 | 1.994 | 100 |
| 0.05 | 1.276 | 53.5 | 0.025 | 1.683 | 84 |
| 0.1 | 1.181 | 49.5 | 0.1 | 1.302 | 65 |
| 0.5 | 0.566 | 23.7 | 0.25 | 0.918 | 46 |
| 1 | 0.404 | 16.9 | 0.5 | 0.68 | 34 |
| 5 | 0.151 | 6.33 | 1 | 0.469 | 24 |
| $IC_{50}$ (ng/ml) | 0.082 | | $IC_{50}$ (ng/ml) | 0.202 | |

$A_{450}$ = absorbance at 450 nm
B = absorbance at 450 nm at $x$ ng/ml standard concentration
$B_0$ = absorbance at 450 nm at 0 ng/ml standard concentration
$IC_{50}$ = standard concentration which produces 50% $B/B_0$
% CR = percentage cross-reactivity based on specificity to ractopamine - this is what is meant by the term "cross-reactivity" in the present specification.

Example 23

Cross Reactivity of Competitive ELISAs for Ractopamine

In order to determine the specificity of the competitive ELISAs for ractopamine, standard solutions of a range of structurally similar β-agonists were prepared in TBST. Employing each series of standards in the ractopamine competitive ELISAs, calibration curves were generated and these were used to determine the cross-reactivity of each immunoassay with these substances. The results of this study are presented in Table 2, cross-reactivity being calculated according to the following formula:

$$\% \ CR = IC_{50, \ ractopamine}/IC_{50, \ CR} \times 100$$

Where % CR is the percentage cross-reactivity, $IC_{50, \ ractopamine}$ is the concentration of ractopamine that causes 50% displacement of signal and $IC_{50, \ CR}$ is the concentration of potential cross-reactant that causes 50% displacement of signal.

TABLE 2

Cross reactivity of the competitive ELISAs for ractopamine

| Compound | Example 15 a) | | Example 15 b) | | Shelver pAb | | Shelver mAb | |
|---|---|---|---|---|---|---|---|---|
| | $IC_{50 \ CR}$ ng/ml | % CR | $IC_{50 \ CR}$ ng/ml | % CR | $IC_{50 \ CR}$ ng/ml | % CR | $IC_{50 \ CR}$ ng/ml | % CR |
| Ractopamine | 0.082 | 100 | 0.202 | 100 | 4.2 | 100 | 2.69 | 100 |
| Dobutamine | 44.2 | 0.186 | >50 | <0.8 | 12.7 | 33 | 50.3 | 5.3 |
| Isoxsuprine | >50 | <0.16 | >50 | <0.6 | 6,200 | 0.1 | 1,391 | 0.2 |
| DL-Isoproterenol | >50 | <0.16 | >50 | <0.5 | >100,000 | <0.01 | NA | NA |
| Ritodrine | >50 | <0.16 | >50 | <0.5 | 577 | 0.8 | 73.8 | 3.6 |
| Salmeterol Xinafoate | >50 | <0.16 | >50 | <0.5 | 1,800 | 0.2 | 1519 | 0.2 |
| Methyl Clenbuterol | >50 | <0.16 | >50 | <0.05 | NA | NA | NA | NA |
| Fenoterol | >50 | <0.16 | >50 | <0.05 | 310 | 1.3 | 2,682 | 0.1 |
| Pirbuterol | >50 | <0.16 | >50 | <0.05 | NA | NA | NA | NA |
| Tulobuterol | >50 | <0.16 | >50 | <0.05 | NA | NA | NA | NA |
| Dopamine | >50 | <0.16 | >50 | <0.01 | NA | NA | NA | NA |
| Salbutamol | >50 | <0.16 | >50 | <0.01 | 79,000 | <0.01 | NA | <0.1 |
| Clenbuterol | >50 | <0.16 | >50 | <0.01 | >100,000 | <0.01 | NA | <0.1 |
| Metaproterenol | >50 | <0.16 | >50 | <0.01 | >100,000 | <0.01 | NA | NA |
| Terbutaline | >50 | <0.16 | >50 | <0.01 | NA | NA | NA | NA |
| Cimaterol | >50 | <0.16 | >50 | <0.01 | NA | NA | NA | NA |

TABLE 2-continued

Cross reactivity of the competitive ELISAs for ractopamine

| Compound | Example 15 a) | | Example 15 b) | | Shelver pAb | | Shelver mAb | |
|---|---|---|---|---|---|---|---|---|
| | $IC_{50\,CR}$ ng/ml | % CR | $IC_{50\,CR}$ ng/ml | % CR | $IC_{50\,CR}$ ng/ml | % CR | $IC_{50\,CR}$ ng/ml | % CR |
| Bamethane | >50 | <0.16 | >50 | <0.01 | 2,900 | 0.1 | 831 | 0.3 |
| (−) Isoproterenol | >50 | <0.16 | >50 | <0.01 | NA | NA | NA | NA |
| Mabuterol | >50 | <0.16 | >50 | <0.01 | NA | NA | NA | NA |

$IC_{50,CR}$ = concentration of potential cross-reactant that causes 50% displacement of signal
% CR = percentage cross-reactivity based on specificity to ractopamine
Shelver pAb = Shelver polyclonal antiserum (Shelver and Smith, Journal of Immunoassay (2000), 21(1))
Shelver mAb = Shelver monoclonal antibody (Shelver et al., J. Agric. Food Chem. 48 (2000))

The data presented in Table 1 indicate that the ractopamine immunoassays developed employing antibodies generated to hapten A and hapten B are highly sensitive with $IC_{50}$ values of 0.082 and 0.202 ng/ml, respectively. These immunoassays are considerably more sensitive than those presented in the prior art. For example, Shelver et al. (2000) reported an $IC_{50}$ of 4.2 ng/ml for their ractopamine EIA. The specificity data presented in Table 2 indicate that the antibodies employed are highly specific for ractopamine. There is negligible cross-reactivity with dobutamine (<0.8%) for both antibodies in the present application, compared with that published in the prior art. For example, Shelver et al reported 33% cross-reactivity with dobutamine for their polyclonal antibody and 5.3% cross-reactivity with dobutamine for their monoclonal antibody.

The ractopamine-derived antibodies from the present invention will therefore yield highly specific results when screening biological samples for the presence of ractopamine.

Example 24

Development of a Competitive ELISA for Isoxsuprine

In a similar manner to that described in Example 22(a), the wells of a 96-well microtiter plate were coated with the IgG fraction of the antiserum raised to immunogen D (hapten D-BSA) (Example 19), isoxsuprine standards were applied at 0, 0.5, 1, 5, 10, 50, 100 and 200 ng/ml and conjugate D (hapten D-HRP) (Example 20) was employed as detection reagent. The data generated are presented in Table 3.

Example 25

Development of a Competitive ELISA for Ritodrine

In a similar manner to that described in Example 22(a), the wells of a 96-well microtiter plate were coated with the IgG fraction of the antiserum raised to immunogen E (hapten E-BSA) (Example 19), ritodrine standards were applied at 0, 1, 5, 10, 50, 100, 500 and 1000 ng/ml and conjugate E (hapten E-HRP) (Example 20) was employed as detection reagent. The data generated are also presented in Table 3.

TABLE 3

Data generated from competitive microtiter plate assays for isoxsuprine and ritodrine, employing antisera generated to immunogen D (hapten D-BSA) (Example 19) and immunogen E (hapten E-BSA) (Example 19).

| Example 24 | | | Example 25 | | |
|---|---|---|---|---|---|
| Isoxsuprine Concentration ng/ml | $A_{450}$ | % $B/B_0$ | Ritodrine Concentration ng/ml | $A_{450}$ | % $B/B_0$ |
| 0 | 2.345 | 100 | 0 | 1.946 | 100 |
| 0.5 | 0.743 | 31.6 | 1 | 1.791 | 92.0 |
| 1 | 0.399 | 17.0 | 5 | 1.602 | 82.3 |
| 5 | 0.158 | 6.7 | 10 | 1.562 | 80.2 |
| 10 | 0.115 | 4.9 | 50 | 1.260 | 64.7 |
| 50 | 0.036 | 1.5 | 100 | 1.088 | 55.9 |
| 100 | 0.032 | 1.3 | 500 | 0.584 | 30.0 |
| 200 | 0.022 | 0.9 | 1000 | 0.440 | 22.6 |
| $IC_{50}$ (ng/ml) | 0.230 | | $IC_{50}$ (ng/ml) | 115.230 | |

$A_{450}$ = absorbance at 450 nm
B = absorbance at 450 nm at x ng/ml standard concentration
$B_0$ = absorbance at 450 nm at 0 ng/ml standard concentration
$IC_{50}$ = standard concentration which produces 50% $B/B_0$ Example 26

Cross Reactivity of Competitive ELISAs for Isoxsuprine and Ritodrine

In a similar manner to that described in Example 23, the cross reactivity of each immunoassay with isoxsuprine, ritodrine, dobutamine and ractopamine was determined. The results of this study are presented in Table 4.

TABLE 4

Cross reactivity of the competitive ELISAs for isoxsuprine (Example 24) and ritodrine (Example 25)

| Compound | Example 24 | | Example 25 | |
|---|---|---|---|---|
| | $IC_{50\,CR}$ ng/ml | % CR | $IC_{50\,CR}$ ng/ml | % CR |
| Isoxsuprine | 0.230 | 100 | 569.7 | 20.2 |
| Ritodrine | >200 | <0.1 | 115.2 | 100 |
| Dobutamine | >200 | <0.1 | >1000 | <5.0 |
| Ractopamine | >200 | <0.1 | >1000 | <0.5 |

$IC_{50\,CR}$ = Concentration of potential cross-reactant that causes 50% displacement of signal
% CR = Percentage cross-reactivity based on specificity to isoxsuprine (Example 24) or ritodrine (Example 25)

This high degree of specificity shown in Examples 23 and 26 has been achieved by targeted derivatisation at a single phenolic hydroxy group of phenethanolamines such as, but not limited to, ractopamine, isoxsuprine and ritodrine and ensures that false positive results are kept to a minimum.

What is claimed:

1. A method of preparing a hapten of Formula I

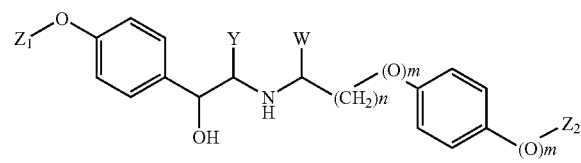

Formula I suitable for use in raising an antibody capable of binding with at least one structural epitope of a phenethanolamine, the method comprising the steps of:

preparing a phenethanolamine derivative of the formula D by reacting octapamine hydrochloride with $Z_1X_1$, in which $Z_1$ is a crosslinker, the crosslinker being —R—$X_2$, in which R is a bivalent link and $X_2$ is a functional group containing at least one hetero-atom capable of linking the R of the crosslinker with a moiety selected from the group comprising an antigenticity-conferring carrier material and a detectable labelling agent, and $X_1$ is a halide; and reacting the phenethanolamine derivative of formula D with a phenylalkylcarbonyl derivative of formula E, in which $Z_2$ is H; Y is independently H or $CH_3$; W is independently H or $CH_3$; n is independently 1 or 2; and m is independently 0 or 1

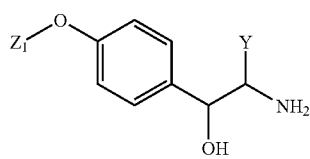

D

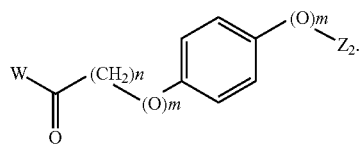

E

2. A method according to claim 1, in which the amine group of the octapamine hydrochloride is temporarily protected with BOC, by reacting the octapamine hydrochloride with di-tert-butyldicarbonate before reacting the BOC-protected octapamine hydrochloride with the $Z_1X_1$, the BOC group being subsequently removed.

3. A method of preparing a hapten of Formula II

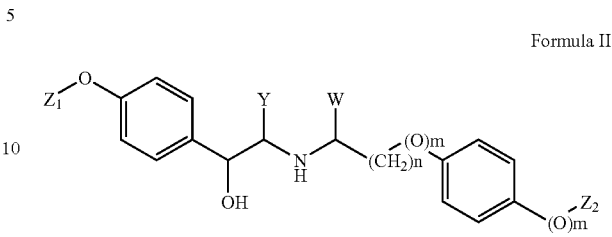

Formula II suitable for use in raising an antibody capable of binding with at least one structural epitope of a phenethanolamine, the method comprising the steps of;

preparing a phenylalkylcarbonyl derivative of the formula E by reacting 4-(4-hydroxyphenyl)-2-butanone with $Z_2X_1$, in which $Z_2$ is a crosslinker, the crosslinker being —R—$X_2$, in which R is a bivalent link and $X_2$ is a functional group containing at least on hetero-atom capable of linking the R of the crosslinker with a moiety selected from the group comprising an antigenicity-conferring material and a detectable labelling agent, and $X_1$ is halide; and reacting a phenethanolamine derivative of formula D, with the phenylalkylcarbonyl derivative of formula E, in which $Z_1$ is H, Y is independently H or $CH_3$; W is independently H or $CH_3$; n is independently 1 or 2; and m is independently 0 or 1

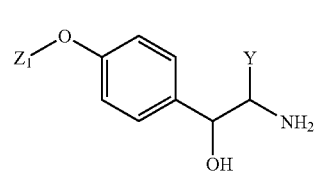

D

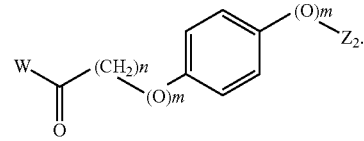

E

4. An immunogen comprising a hapten and an antigenicity-conferring carrier material, wherein said hapten has the formula of Formula I

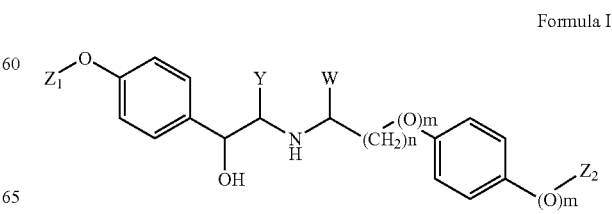

Formula I wherein said hapten is prepared by the steps of:
preparing a phenethanolamine derivative of the formula D by reacting octopamine hydrochloride with $Z_1X_1$, in which $Z_1$ is a crosslinker, the crosslinker being —R—$X_2$, in which R is a bivalent link and $X_2$ is a functional group containing at least on hetero-atom capable of linking the R of the crosslinker with said antigenicity-conferring material, and $X_1$ is a halide; and
reacting the phenethanolamine derivative of formula D with a phenylalkylcarbonyl derivative of formula E, in which $Z_2$ is H; Y is independently H or $CH_3$; is independently H or $CH_3$; n is independently 1 or 2; and m is independently 0 or 1,

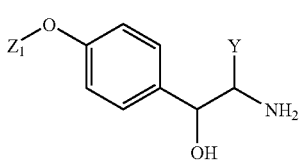
D

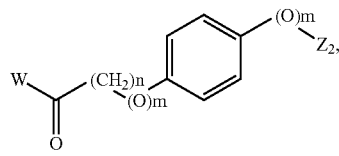
E and wherein said crosslinker links said hapten to said antigenicity-conferring carrier material at a single phenolic hydroxyl group of said hapten.

5. An immunogen comprising a hapten and an antigenicity-conferring carrier material, wherein said hapten has the formula of Formula II

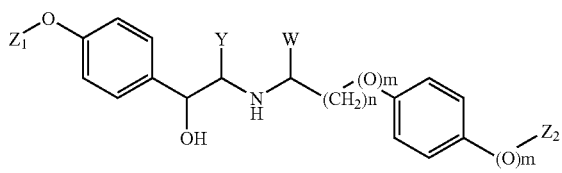
Formula II wherein said hapten is prepared by the steps of:
preparing a phenylalkylcarbonyl derivative of the formula E by reacting 4-(4-hydroxyphenyl)-2-butanone with $Z_2X_1$, in which $Z_2$ is a crosslinker, the crosslinker being —R—$X_2$, in which R is a bivalent link and $X_2$ is a functional group containing at least one hetero-atom capable of linking the R of the crosslinker with said antigenicity-conferring carrier material, and $X_1$ is a halide;
reacting a phenethanolamine derivative of formula D, with the phenylalkylcarbonyl derivative of formula E, in which $Z_1$ is H, Y is independently H or $CH_3$; W is independently H or $CH_3$; n is independently 1 or 2; and m is independently 0 or 1

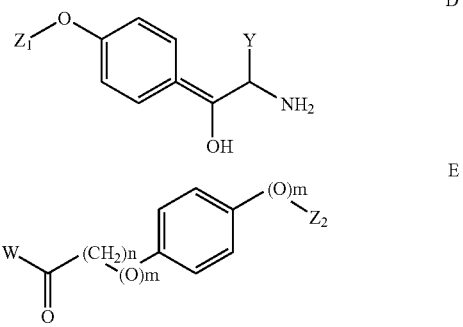
D

E and wherein said crosslinker links said hapten to said antigenicity-conferring carrier material at a single phenolic hydroxyl group of said hapten.

6. An antibody raised against an immunogen, wherein said immunogen comprises a hapten and an antigenicity-conferring carrier material, wherein said hapten has the formula of Formula I

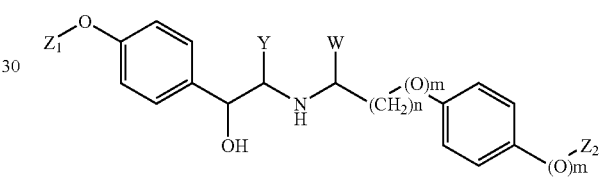
Formula I wherein said hapten is prepared by the step of:
preparing a phenethanolamine deriavative of the formula D by reacting octopamine hydrochloride with $Z_1X_1$, in which $Z_1$ is a crosslinker, the crosslinker being —R—$X_2$, in which R is a bivalent link and $X_2$ is a functional group containing at least one hetero-atom capable of linking the R of the crosslinker with said antigenicity-conferring carrier material, and $X_1$ is a halide; and
reacting the phenethanolamine derivative of formula D with a phenylalkylcarbonyl derivative of formula E, in which $Z_2$ is H; Y is independently H or $CH_3$; W is independently H or $CH_3$; n is independently 1 or 2; and m is independently 0 or 1

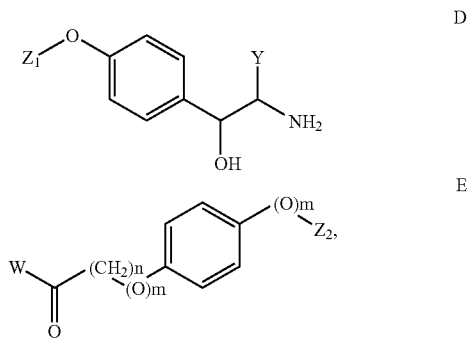
D

E wherein said crosslinker links said hapten to said antigenicity-conferring carrier material at a single phenolic hydroxyl group of said hapten; wherein said antibody specifically binds to said immunogen, said antibody being capable of binding with at least one structural epitope of a phenethanolamine, and wherein the antibody shows a cross reactivity, when compared to 100% for ractopamine, isoxsuprine and ritodrine, of less than 5% for dobutamine.

7. An antibody raised against an immumogen, wherein said immunogen comprises a hapten and an antigenicity-conferring carrier material, wherein said hapten has the formula of Formula II

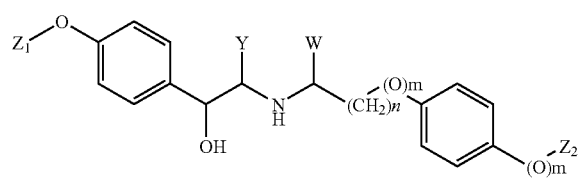

Formula II wherein said hapten is prepared by the steps of:
preparing a phenylalkylcarbonyl derivative of the formula E by reacting 4-(4-hydroxyphenyl)-2-butanone with $Z_2X_1$, in which $Z_2$ is a crosslinker, the crosslinker being —R—$X_2$, in which R is a bivalent link and $X_2$ is a functional group containing at least one hetero-atom capable of linking the R of the crosslinker with said antigenicity-conferring material, and $X_1$ is a halide;

reacting a phenethanolamine derivative of formula D, with the phenylalkylcarbonyl derivative of formula E, in which $Z_1$ is H, Y is independently H or $CH_3$; W is independently H or $CH_3$; n is independently 1 or 2; and m is independently 0 or 1

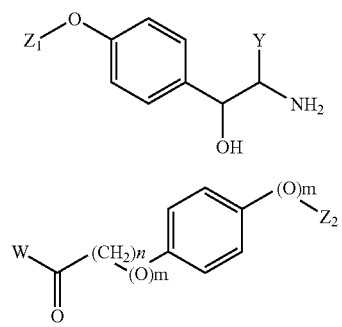

wherein said crosslinker links said hapten to said antigenicity-conferring carrier material at a single phenolic hydroxyl group of said hapten; wherein said antibody specifically binds to said immunogen, said antibody being capable of binding with at least one structural epitope of a phenethanolamine, and wherein the antibody shows a cross reactivity, when compared to 100% for ractopamine, isoxsuprine and ritodrine, of less than 5% for dobutamine.

8. A conjugate comprising a hapten and a detectable labelling agent, wherein said hapten has the formula of Formula I

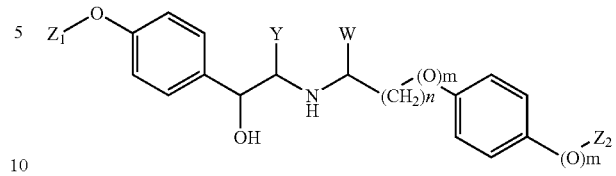

Formula I wherein said hapten is prepared by the steps of:
preparing a phenethanolamine derivative of the formula D by reacting octopamine hydrochloride with $Z_1X_1$, in which $Z_1$ is a crosslinker, the crosslinker being —R—$X_2$, in which R is a bivalent link and $X_2$ is a functional group containing at least one hetero-atom capable of linking the R of the crosslinker with said detectable labelling agent, and $X_1$ is a halide; and reacting the phenethanolamine derivative of formula D with a phenylalkylcarbonyl derivative of formula E, in which $Z_2$ is H; Y is independently H or $CH_3$; W is independently H or $CH_3$; n is independently 1 or 2; and m is independently 0 or 1

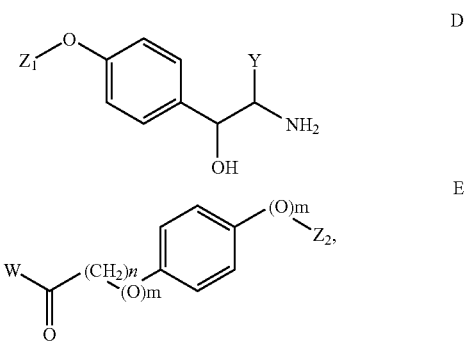

wherein said crosslinker links said hapten to said detectable labelling agent at a single phenolic hydroxyl group of said hapten.

9. A conjugate comprising a hapten and a detectable labelling agent, wherein said hapten has the formula of Formula II

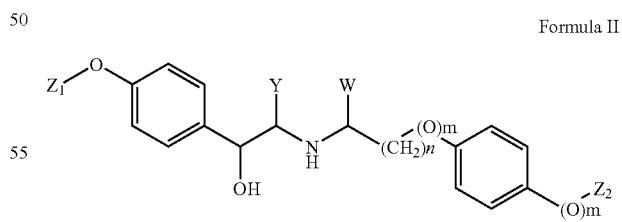

Formula II wherein said hapten is prepared by the steps of:
preparing a phenylalkylcarbonyl derivative of the formula E by reacting 4-(4-hydroxyphenyl)-2-butanone with $Z_2X_1$, in which $Z_2$ is a crosslinker, the crosslinker being —R—$X_2$, in which R is a bivalent link and $X_2$ is functional group containing at least one hetero-atom capable of linking the R of the crosslinker with a detectable labelling agent, and $X_1$ is a halide;

reacting a phenethanolamine derivative of formula D, with the phenylalkylcarbonyl derivative of formula E, in which $Z_1$ is H, Y is independently H or $CH_3$; W is independently H or $CH_3$; n is independently 1 or 2; and m is independently 0 or 1

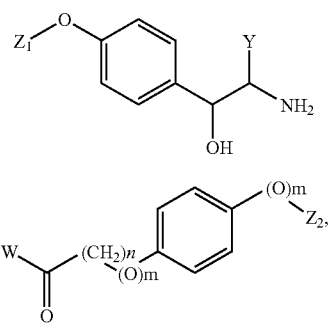

D

E wherein said crosslinker links said hapten to said detectable labelling agent as a single phenolic hydrroxyl group of said hapten.

10. A method for detecting or determining a phenethanolamine in a sample, the method comprising:
(a) contacting the sample with at least one conjugate, and at least one antibody of claim 6; wherein said conjugate comprises a hapten and a detectable labelling agent wherein said hapten has the formula of Formula I

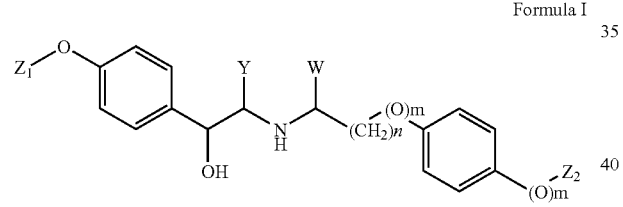

Formula I and said hapten is prepared by the steps of:
preparing a phenethanolamine derivative of the formula D by reacting octopamine hydrochloride with $Z_1X_1$, in which $Z_1$ is a crosslinker, the crosslinker being —R—$X_2$, in which R is a bivalent link and $X_2$ is a functional group containing at least one heteroatom capable of linking the R of the crosslinking with said detectable labeling agent, and $X_1$ is a halide; and
reacting the phenethanolamine derivative of formula D with a phenylalkylcarbonyl derivative of formula E, in which $Z_2$ is H; Y is independently H or $CH_3$; W is independently H or $CH_3$; n is independently 1 or 2; and m is independently 0 or 1

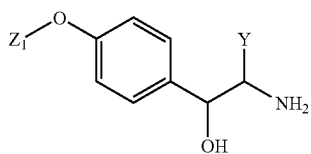

D

-continued

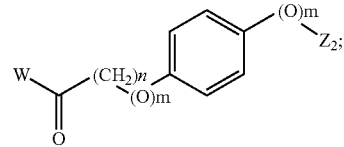

E wherein said crosslinker links said hapten to said detectable labelling agent at a single phenolic hydroxyl group of said hapten; and
(b) detecting or determining bound conjugate; and deducing from the calibration curve the presence of, or the amount of, the phenethanolamine in the sample.

11. A method for detecting or determining a phenethanolamine in a sample, the method comprising:
(a) contacting the sample with at least one conjugate, and at least one antibody of claim 7; wherein said conjugate comprises a hapten and a detectable labeling agent wherein said hapten has the formula of Formula I

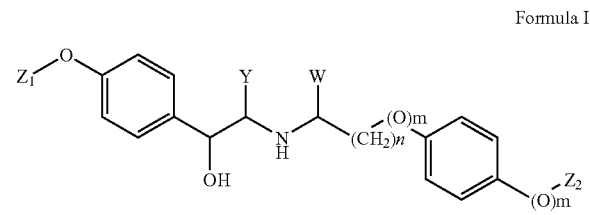

Formula I and said hapten by the steps of:
preparing a phenethanolamine derivative of the formula D by reacting octopamine hydrochloride with $Z_1X_1$, in which $Z_1$ is a crosslinker, the crosslinker being —R—$X_2$, in which R is a bivalent link and $X_2$ is a functional group containing at least one heteroatom capable of linking the R of the crosslinker with said detectable labelling agent, and $X_1$ is a halide; and
reacting the phenethanolamine derivative of formula D with a phenylalkylcarbonyl derivative of formula E, in which $Z_2$ is H; Y is independently H or $CH_3$; W is independently H or $CH_3$; n is independently 1 or 2; and m is independently 0 or 1

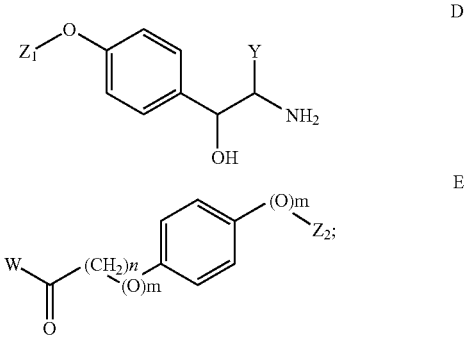

wherein said crosslinker links said hapten to said detectable labelling agent at a single phenolic hydroxyl group of said hapten; and (b) detecting or determining bound conjugate; and deducing from the calibration curve the presence of, or the amount of, the phenethanolamine in the sample.

12. A method for detecting or determining a phenethanolamine in a sample, the method comprising:
(a) contacting the sample with at least one conjugate, and at least one antibody of claim 6, wherein said conjugate comprises a hapten and a detectable labelling agent, wherein said hapten has the formula of Formula II

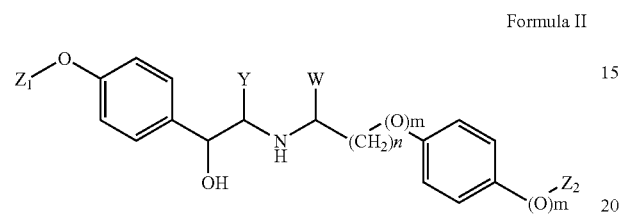

Formula II wherein said hapten is prepared by the steps of:
preparing a phenylalkylcarbonyl derivative of the formula E by reacting 4-(4-hydroxyphenyl)-2-butanone with $Z_2X_1$, in which $Z_2$ is a crosslinker, the crosslinker being —R—$X_2$, in which R is a bivalent link and $X_2$ is a functional group containing at least on hetero-atom capable of linking the R of the crosslinker with said detectable labelling agent, and $X_1$ is halide;
reacting a phenethanolamine derivative of formula D, with the phenylalkylcarbonyl derivative of formula E, in which $Z_1$ is H, Y is independently H or $CH_3$; W is independently H or $CH_3$; n is independently 1 or 2; and m is independently 0 or 1

D

E wherein said crosslinker links said hapten to said detectable labelling agent at a single phenolic hydroxyl group of said hapten; and
(b) detecting or determining bound conjugate; and deducing from the calibration curve the presence of, or the amount of, the phenethanolamine in the sample.

13. A method for detecting or determining a phenethanolamine in a sample, the method comprising:
(a) contacting the sample with at least one conjugate and at least one antibody of claim 7, wherein said conjugate comprises a hapten and a detectable labelling agent, wherein said hapten has the formula of Formula II Formula II wherein said hapten is prepared by the steps of:
preparing a phenylalkylcarbonyl derivative of the formula E by reacting 4-(4-hydroxyphenyl)-2-butanone with $Z_2X_1$, in which $Z_2$ is a crosslinker, the crosslinker being —R—$X_2$, in which R is a bivalent link and $X_2$ is a functional group containing at least on hetero-atom capable of linking the R of the crosslinker with said detectable labelling agent, and $X_1$ is halide;
reacting a phenethanolamine derivative of formula D, with the phenylalkylcarbonyl derivative of formula E, in which $Z_1$ is H, Y is independently H or $CH_3$; W is independently H or $CH_3$; n is independently 1 or 2; and m is independently 0 or 1

D

E wherein said crosslinker links said hapten to said detectable labelling agent at a single phenolic hydroxyl group of said hapten; and
(b) detecting or determining bound conjugate; and deducing from the calibration curve the presence of, or the amount of, the phenethanolamine in the sample.

14. A kit for detecting or determining a phenethanolamine, the kit comprising at least one conjugate; and at least one antibody of claim 6, wherein said conjugate comprises a hapten and a detectable labelling agent wherein said hapten has the formula of Formula I Formula I and said hapten is prepared by the steps of:
preparing a phenethanolamine derivative of the formula D by reacting octopamine hydrochloride with $Z_1X_1$, in which $Z_1$ is a crosslinker, the crosslinker being —R—$X_2$, in which R is a bivalent link and $X_2$ is a functional group containing at least one hetero-atom capable of linking the R of the crosslinker with said detectable labelling agent, and $X_1$ is a halide; and reacting the phenethanolamine derivative of formula D with a phenylalkylcarbonyl derivative of formula E, in which $Z_2$ is H; Y is independently H or $CH_3$; W is independently H or $CH_3$; n is independently 1 or 2; and m is independently 0 or 1

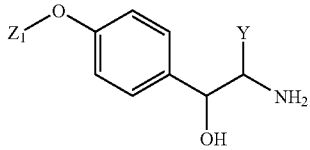

D

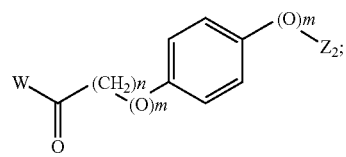

E wherein said crosslinker links said hapten to said detectable labelling agent at a single phenolic hydroxyl group of said hapten.

15. A kit for detecting or determining a phenethanolamine, the kit comprising at least one conjugate and at least one antibody of claim 7, wherein said conjugate comprises a hapten and a detectable labelling agent wherein said hapten has the formula of Formula I Formula I

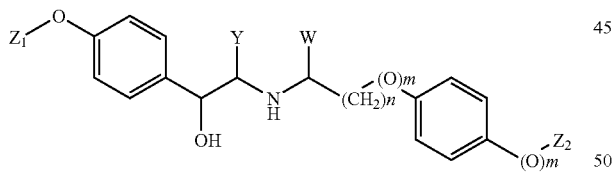

and said hapten is prepared by the steps of:

preparing a phenethanolamine derivative of the formula D by reacting octopamine hydrochloride with $Z_1X_1$, in which $Z_1$ is a crosslinker being —R—$X_2$, in which R is a bivalent link and $X_2$ is a functional group containing at least one hetero-atom capable of linking the R of the crosslinker with said detectable labelling agent, and $X_1$ is a halide; and reacting the phenethanolamine derivative of formula D with a phenylalkylcarbonyl derivative of formula E, in which $Z_2$ is H; Y is independently H or $CH_3$; W is independently H or $CH_3$; n is independently 1 or 2; and m is independently 0 or 1

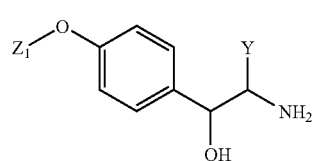

D

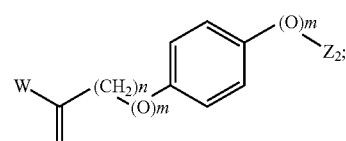

E wherein said crosslinker links said hapten to said detectable labelling agent at a single phenolic hydroxyl group of said hapten.

16. A kit for detecting or determining a phenethanolamine, the kit comprising at least one conjugate and at least one antibody of claim 6, wherein said conjugate comprises a hapten and a detectable labelling agent, wherein said hapten has the formula of Formula II Formula II

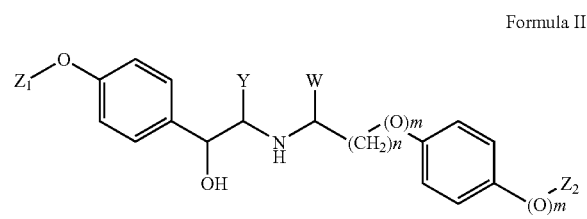

wherein said hapten is prepared by the steps of:

preparing a phenylalkylcarbonyl derivative of the formula E by reacting 4-(4-hydroxyphenyl)-2-butanone with $Z_2X_1$, in which $Z_2$ is a crosslinker, the crosslinker being —R—$X_2$, in which R is a bivalent link and $X_2$ is a functional group containing at least on hetero-atom capable of linking the R of the crosslinker with said detectable labelling agent, and $X_1$ is halide;

reacting the phenethanolamine derivative of formula D, with the phenylalkylcarbonyl derivative of formula E, in which $Z_1$ is H, Y is independently H or $CH_3$; W is independently H or $CH_3$; n is independently 1 or 2; and m is independently 0 or 1

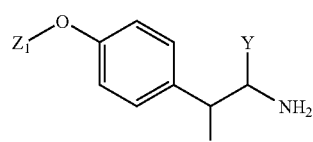

D

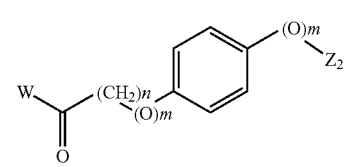

E wherein said crosslinker links said hapten to said detectable labelling agent at a single phenolic hydroxyl group of said hapten.

17. A kit for detecting or determining a phenethanolamine, the kit comprising at least one conjugate and at least one antibody of claim 7, wherein said conjugate comprises a hapten and a detectable labelling agent, wherein said hapten has the formula of Formula II Formula II

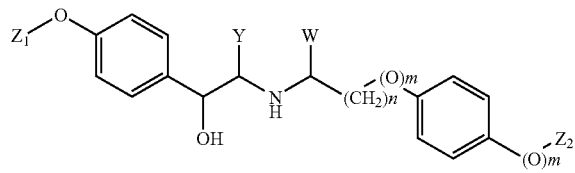

and said hapten is prepared by the steps of:
preparing a phenylalkylcarbonyl derivative of the formula E by reacting 4-(4-hydroxyphenyl)-2-butanone with $Z_2X_1$, in which $Z_2$ is a crosslinker, the crosslinker being —R—$X_2$, in which R is a bivalent link and $X_2$ is a functional group containing at least on hetero-atom capable of linking the R of the crosslinker with said detectable labelling agent, and $X_1$ is halide;
reacting the phenethanolamine derivative of formula D, with the phenylalkylcarbonyl derivative of formula E, in which $Z_1$ is H, Y is independently H or $CH_3$; W is independently H or $CH_3$; n is independently 1 or 2; and m is independently 0 or 1

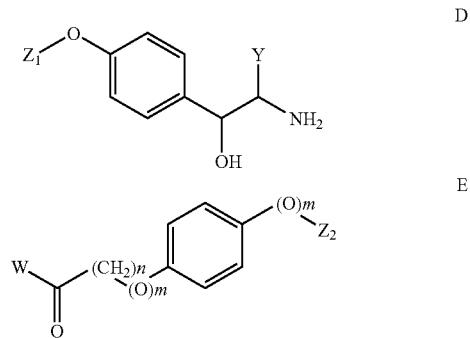

wherein said crosslinker links said hapten to said detectable labelling agent at a single phenolic hydroxyl group of said hapten.

18. The immunogen of claim 4 or 5, in which R is selected from the group comprising a substituted or unsubstituted, straight or branched chain, saturated or unsaturated alkylene group and a substituted or unsubstituted arylene group and $X_2$ is selected from the group comprising a carboxylic acid or an ester thereof; an amine; a maleimide, a halocarboxylic acid or an ester thereof, an aldehyde, a dithiopyridyl group a vinylsulphone group, and a thiocarboxylic acid or an ester thereof.

19. An antibody raised against the immunogen of claim 18 that specifically binds to the immunogen of claim 23, the antibody being capable of binding with at least one structural epitope of a phenethanolamine, wherein the antibody shows a cross reactivity, when compared to 100% for ractopamine, isoxsuprine and ritodrine, of less than 5% for dobutamine.

20. The conjugate of claim 8 or 9, in which R is selected from the group comprising a substituted or unsubstituted, straight or branched chain, saturated or unsaturated alkylene group and a substituted or unsubstituted arylene group and $X_2$ is selected from the group comprising a carboxylic acid or an ester thereof; an amine; a maleimide, a halocarboxylic acid or an ester thereof, an aldehyde, a dithiopyridyl group a vinylsulphone group, and a thiocarboxylic acid or an ester thereof.

21. The immunogen of claim 18, in which R is selected from a $C_{1-5}$ substituted or unsubstituted, straight chain, saturated alkylene group and a $C_{1-3}$ substituted or unsubstituted, straight chain, saturated alkylene group.

22. An antibody raised against the immunogen of claim 18 wherein R is selected from a $C_{1-5}$ substituted or unsubstituted, straight chain, saturated alkylene group and a $C_{1-3}$ substituted or unsubstituted, straight chain, saturated alkylene group, the antibody being capable of binding with at least one structural epitope of a phenethanolamine, wherein the antibody shows a cross reactivity, when compared to 100% for ractopamine, isoxsuprine and ritodrine, of less than 5% for dobutamine.

23. The conjugate of claim 20, in which R is selected from a $C_{1-5}$ substituted or unsubstituted, straight chain, saturated alkylene group and a $C_{1-3}$ substituted or unsubstituted, straight chain, saturated alkylene group.

24. A method for detecting or determining a phenethanolamine in a sample, the method comprising:
(a) contacting the sample with at least one conjugate and at least one antibody of claim 22, wherein said conjugate comprises a hapten and a detectable labeling agent, wherein said hapten has the formula of Formula I Formula I wherein said hapten is prepared by the steps of:
preparing a phenethanolamine derivative of the formula D by reacting octopamine hydrochloride with $Z_1X_1$, in which;
$Z_1$ is a crosslinker, the crosslinker being —R—$X_2$, in which R is selected from a $C_{1-5}$ substituted or unsubstituted, straight chain, saturated alkylene group; and a $C_{1-3}$ substituted or unsubstituted, straight chain, saturated alkylene group; which serves as a bivalent link;
$X_2$ is a functional group containing at least one hetero-atom capable of linking the R of the crosslinker with said detectable labelling agent, and is selected from the group comprising a carboxylic acid or an ester thereof; an amine; a maleimide, a halocarboxylic acid or an ester thereof, an aldehyde, a dithiopyridyl group, a vinylsulphone group, and a thiocarboxylic acid or an ester thereof; and $X_1$ is a halide;
and
reacting the phenethanolamine derivative of formula D with a phenylalkylcarbonyl derivative of formula E, in which $Z_2$ is H; Y is independently H or $CH_3$; W is independently H or $CH_3$; n is independently 1 or 2; and m is independently 0 or 1;

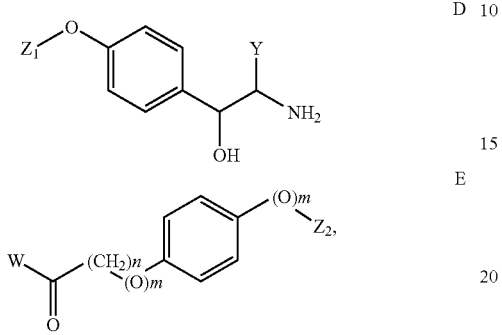

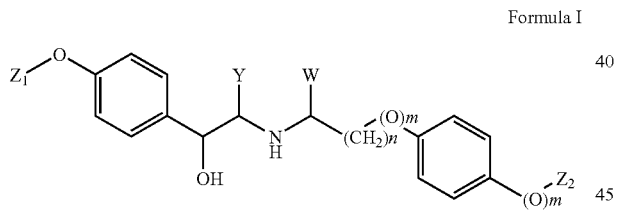

wherein said crosslinker links said hapten to said detectable labelling agent at a single phenolic hydroxyl group of said hapten;
and
(b) detecting or determining bound conjugate; and deducing from the calibration curve the presence of, or the amount of, the phenethanolamine in the sample.

25. A kit for detecting or determining a phenethanolamine, the kit comprising at least one conjugate and at least one antibody of claim 22, wherein said conjugate comprises a hapten and a detectable labelling agent, wherein said hapten has the formula of Formula I Formula I

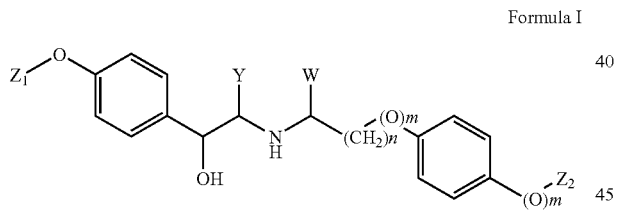

wherein said hapten is prepared by the steps of:
preparing a phenethanolamine derivative of the formula D by reacting octopamine hydrochloride with $Z_1X_1$, in which;
$Z_1$ is a crosslinker, the crosslinker being —R—$X_2$, in which R is selected from a $C_{1-5}$ substituted or unsubstituted, straight chain, saturated alkylene group; and a $C_{1-3}$ substituted or unsubstituted, straight chain, saturated alkylene group; which serves as a bivalent link;
$X_2$ is a functional group containing at least one hetero-atom capable of linking the R of the crosslinker with said detectable labelling agent, and is selected from the group comprising a carboxylic acid or an ester thereof; an amine; a maleimide, a halocarboxylic acid or an ester thereof, an aldehyde, a dithiopyridyl group, a vinylsulphone group, and a thiocarboxylic acid or an ester thereof; and
$X_1$ is a halide;
and reacting the phenethanolamine of formula D with a phenylalkylcarbonyl derivative of formula E, in which $Z_2$ is H; Y is independently H or $CH_3$; W is independently H or $CH_3$; n is independently 1 or 2; and m is independently 0 or 1;

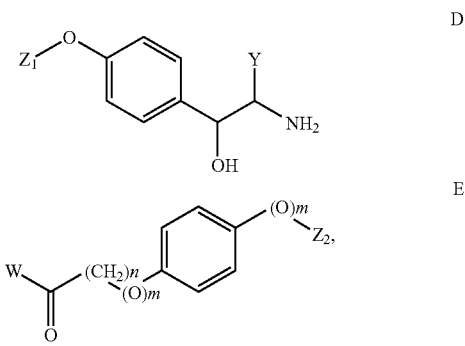

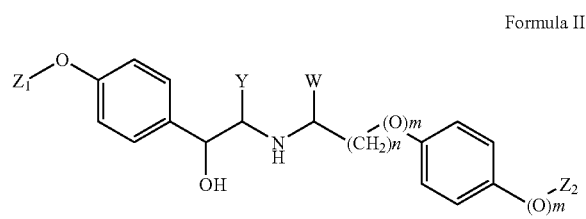

wherein said crosslinker links said hapten to said detectable labelling agent at a single phenolic hydroxyl group of said hapten.

26. A method for detecting or determining a phenethanolamine in a sample, the method comprising:
(a) contacting the sample with at least one conjugate and at least one antibody of claim 22, wherein said conjugate comprises a hapten and a detectable labeling agent, wherein said hapten has the formula of Formula II Formula II

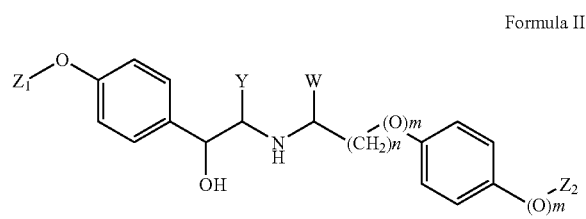

wherein said hapten is prepared by the steps of:
preparing a phenylalkylcarbonyl derivative of the formula E by reacting 4-(4-hydroxyphenyl)-2-butanone with $Z_2X_1$, in which
$Z_2$ is a crosslinker, the crosslinker being —R—$X_2$, in which R is selected from a $C_{1-5}$ substituted or unsubstituted, straight chain, saturated alkylene group; and a $C_{1-3}$ substituted or unsubstituted, straight chain, saturated alkylene group; which serves as a bivalent link;
$X_2$ is a functional group containing at least one hetero-atom capable of linking the R of the crosslinker with said detectable labelling agent, and is selected from the group comprising a carboxylic acid or an ester thereof; an amine; a maleimide, a halocarboxylic acid or an ester thereof, an aldehyde, a dithiopyridyl group, a vinylsulphone group, and a thiocarboxylic acid or an ester thereof; and
$X_1$ is a halide;
and
reacting the phenethanolamine of formula D with a phenylalkylcarbonyl derivative of formula E, in which $Z_1$ is H; Y is independently H or $CH_3$; W is independently H or CH$_3$; n is independently 1 or 2; and m is independently 0 or 1;

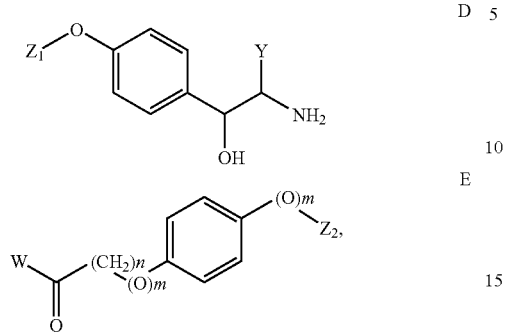

wherein said crosslinker links said hapten to said detectable labelling agent at a single phenolic hydroxyl group of said hapten;
(b) detecting or determining bound conjugate; and
(c) deducing from the calibration curve the presence of, or the amount of, the phenethanolamine in the sample.

27. A kit for detecting or determining a phenethanolamine, the kit comprising at least one conjugate and at least one antibody of claim 22, wherein said conjugate comprises a hapten and a detectable labelling agent, wherein said hapten has the formula of Formula II Formula II

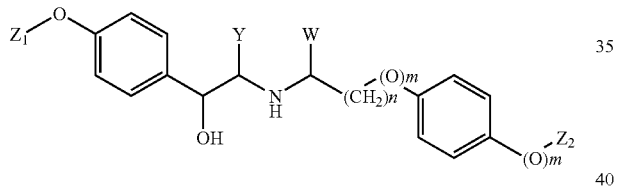

wherein said hapten is prepared by the steps of:
preparing a phenylalkylcarbonyl derivative of the formula E by reacting 4-(4-hydroxyphenyl)-2-butanone with Z$_2$X$_1$, in which Z$_2$ is a crosslinker, the crosslinker being —R—X$_2$, in which R is selected from a C$_{1-5}$ substituted or unsubstituted, straight chain, saturated alkylene group; and a C$_{1-3}$ substituted or unsubstituted, straight chain, saturated alkylene group; which serves as a bivalent link;

X$_2$ is a functional group containing at least one heteroatom capable of linking the R of the crosslinker with said detectable labelling agent, and is selected from the group comprising a carboxylic acid or an ester thereof; an amine; a maleimide, a halocarboxylic acid or an ester thereof, an aldehyde, a dithiopyridyl group, a vinylsulphone group, and a thiocarboxylic acid or an ester thereof; and X$_1$ is a halide;

and reacting the phenethanolamine of formula D with a phenylalkylcarbonyl derivative of formula E, in which Z$_1$ is H; Y is independently H or CH$_3$; W is independently H or CH$_3$; n is independently 1 or 2; and m is independently 0 or 1;

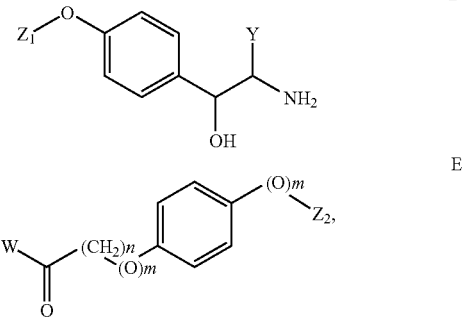

wherein said crosslinker links said hapten to said detectable labelling agent at a single phenolic hydroxyl group of said hapten.

* * * * *